United States Patent
Reiner et al.

(10) Patent No.: US 10,450,256 B2
(45) Date of Patent: Oct. 22, 2019

(54) RENEWABLE KETONE WAXES WITH UNIQUE CARBON CHAIN LENGTHS AND POLARITIES

(71) Applicant: ExxonMobil Research and Engineering Company, Annandale, NJ (US)

(72) Inventors: Virginia M. Reiner, Summit, NJ (US); Michel Daage, Hellertown, NJ (US); Kun Wang, Bridgewater, NJ (US); Sarvesh K. Agrawal, Spring, TX (US); Frank C. Wang, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/137,887

(22) Filed: Sep. 21, 2018

(65) Prior Publication Data

US 2019/0106371 A1    Apr. 11, 2019

Related U.S. Application Data

(60) Provisional application No. 62/568,980, filed on Oct. 6, 2017.

(51) Int. Cl.

| | | |
|---|---|---|
| *C07C 45/00* | (2006.01) | |
| *C11C 3/00* | (2006.01) | |
| *C11C 5/00* | (2006.01) | |
| *C07C 45/67* | (2006.01) | |
| *B01J 23/04* | (2006.01) | |
| *B01J 23/10* | (2006.01) | |
| *B01J 29/04* | (2006.01) | |
| *B01J 29/84* | (2006.01) | |
| *C07C 45/48* | (2006.01) | |
| *C07C 49/203* | (2006.01) | |
| *C09D 191/06* | (2006.01) | |
| *C07C 45/80* | (2006.01) | |
| *C07C 45/82* | (2006.01) | |

(52) U.S. Cl.
CPC ............. *C07C 45/673* (2013.01); *B01J 23/04* (2013.01); *B01J 23/10* (2013.01); *B01J 29/049* (2013.01); *B01J 29/84* (2013.01); *C07C 45/48* (2013.01); *C07C 49/203* (2013.01); *C09D 191/06* (2013.01); *C11C 3/00* (2013.01); *C11C 5/002* (2013.01); *C07C 45/80* (2013.01); *C07C 45/82* (2013.01)

(58) Field of Classification Search
CPC .............................. C07C 45/673; C07C 45/48
See application file for complete search history.

(56) References Cited

U.S. PATENT DOCUMENTS

| | | |
|---|---|---|
| 4,314,915 A | 2/1982 | Wiegers et al. |
| 4,411,829 A | 10/1983 | Schulte-Elte et al. |
| 4,434,306 A | 2/1984 | Kobayashi et al. |
| 4,534,961 A | 8/1985 | Liff |
| 4,614,625 A | 9/1986 | Wilson |
| 6,063,144 A | 5/2000 | Calzada et al. |
| 6,824,572 B2 | 11/2004 | Murphy |
| 7,128,766 B2 | 10/2006 | Murphy et al. |
| 7,138,111 B2 | 11/2006 | Loginova et al. |
| 7,731,767 B2 | 6/2010 | Tao |
| 8,048,290 B2 | 11/2011 | Knuuttila et al. |
| 8,053,614 B2 | 11/2011 | Aalto et al. |
| 8,157,873 B2 | 4/2012 | Murphy et al. |
| 8,202,329 B2 | 6/2012 | Murphy et al. |
| 8,362,125 B2 | 1/2013 | Gong et al. |
| 8,529,924 B2 | 9/2013 | Murphy et al. |
| 8,652,221 B2 | 2/2014 | Uptain et al. |
| 9,587,180 B2 | 3/2017 | Roberts et al. |
| 2005/0053636 A1 | 3/2005 | von der Fecht et al. |
| 2006/0275247 A1 | 12/2006 | Helman et al. |
| 2007/0249771 A1 | 10/2007 | Paul et al. |
| 2010/0021411 A1 | 1/2010 | Bosch et al. |
| 2013/0178640 A1 | 7/2013 | Mujkic et al. |
| 2014/0024869 A1 | 1/2014 | Roberts et al. |
| 2014/0142356 A1 | 5/2014 | Roberts et al. |
| 2014/0171699 A1 | 6/2014 | Wang et al. |
| 2015/0018588 A1 | 1/2015 | Myllyoja et al. |
| 2018/0010061 A1 | 1/2018 | Reiner et al. |

FOREIGN PATENT DOCUMENTS

| | | |
|---|---|---|
| EP | 0457665 A1 | 11/1991 |
| WO | 2017162638 A1 | 9/2017 |

OTHER PUBLICATIONS

The International Search Report and Written Opinion of PCT/US2018/052150 dated Dec. 21, 2018.

*Primary Examiner* — Sikarl A Witherspoon
(74) *Attorney, Agent, or Firm* — Amanda K. Norwood

(57) ABSTRACT

The present disclosure provides ketone waxes, methods of forming ketone waxes, and compositions comprising ketone waxes. In at least one embodiment, a ketone wax is provided. The ketone wax includes about 50 wt % or greater $C_{40}$-$C_{90}$ ketone content; about 50 wt % or greater of the ketone wax has a boiling point of 961° F. or greater; and a paraffins content of less than about 10 wt %, as determined by 2-dimensional gas chromatography. In at least one embodiment, a method for forming a $C_{40}$-$C_{90}$ ketone wax includes exposing a feed stock to a basic catalyst under conditions suitable for coupling unsaturated carbon chains from the feed to form a composition including a ketone wax, oligomerizing the ketone wax to form a ketone wax having $C_{40}$-$C_{90}$ ketone wax, and distilling and/or extracting the oligomerized ketone wax to provide a $C_{40}$-$C_{90}$ ketone wax of the present disclosure.

26 Claims, 11 Drawing Sheets

RENEWABLE KETONE WAXES WITH UNIQUE CARBON CHAIN LENGTHS AND POLARITIES

CROSS-REFERENCE TO RELATED APPLICATIONS

This application claims priority to U.S. Provisional Application Ser. No. 62/568,980 filed Oct. 6, 2017, which is herein incorporated by reference in its entirety.

FIELD

The present disclosure provides ketone waxes, methods of forming ketone waxes, and compositions comprising ketone waxes.

BACKGROUND

Waxes are organic compounds that have long alkyl chains. Animal waxes, vegetable waxes, and petroleum waxes are derived from natural sources. The basic structural unit of natural oils and fats, for example, is a triglyceride, which is an ester of glycerol with three fatty acid molecules having the structure below:

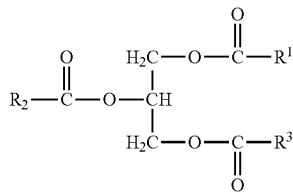

wherein $R_1$, $R_2$, and $R_3$ represent $C_4$-$C_{30}$ hydrocarbon chains, some of which have unsaturation. Fatty acids are carboxylic acids containing long linear hydrocarbon chains. Lengths of the hydrocarbon chains most commonly are 18 carbons ($C_{18}$). $C_{18}$ fatty acids are typically bonded to the middle hydroxyl group of glycerol. Typical carbon numbers of the fatty acids linked to the two other hydroxyl groups are even numbers, being between $C_{14}$ and $C_{22}$. Waxes from natural sources account for 87% of the worldwide wax market. However, for environmental, economical, and regulatory reasons, it is of interest to produce waxes from renewable sources. Synthetic waxes, derived from petroleum or natural gas (a GTL process), are long-chain hydrocarbons lacking functional groups. Synthetic waxes account for 10% of the worldwide wax market.

The renewable waxes derived from animal and vegetable sources typically have a mixture of hydrocarbons, alcohols, free acids and esters. These vegetable and animal based waxes account for only 3% of the global wax market. Recently, there has been a growing demand for renewable waxes as a result of a declining supply of petroleum based waxes, increased paraffin wax prices, and a growing consumer preference for bio-derived products. Natural renewable waxes, however, such as bee's wax, are very expensive.

Microcrystalline waxes/petrolatum waxes derived from fossil fuel sources are widely used in adhesives, coatings, cosmetics and personal care products. The branched structure of the carbon chain backbone in such waxes allows oil molecules to be incorporated into the crystal lattice structure. For use in candles, current approaches to incorporate renewable waxes include mixing of partially hydrogenated, refined and bleached triglyceride (mainly from soybean oil) with fully hydrogenated natural oils and/or free fatty acids. This will lead to a candle wax composition wherein the carbon chain length of the renewable wax molecule is limited to $C_{14}$-$C_{22}$ chains, depending on the source of the triglyceride oil. These wax molecules also have a polarity but are heavily crystalline and may frequently cause highly polar compounds, such as candle scent compounds to be excreted to the outer edges of the candle. Also, such small molecular weight waxes derived from renewable sources do not have adequate properties similar to microcrystalline waxes (such as high viscosity, oil content etc.) to be suitable in several adhesive, coatings and personal care product applications.

A further approach towards renewable wax is the metathesis of vegetable oils leading to dimers and trimers of triglycerides. A disadvantage to this approach is the high oxygen content of the wax, as each triglyceride unit contains 3 ester bonds, averaging to an oxygen content of approximately 9-12 wt %. Although polar, these compounds do not possess enough nonpolar character for wide use in a variety of applications involving polar waxes, for example, in adhesives, candles or personal care products.

Accordingly, there is a need for novel polar waxes derived from renewable sources, particularly to substitute high molecular weight microcrystalline waxes in the $C_{40}$-$C_{90}$ carbon chain length range, methods of forming polar waxes, and compositions comprising polar waxes.

References of interest include: U.S. Pat. No. 6,824,572 A1; U.S. Pat. No. 7,128,766 A1; U.S. Pat. No. 8,202,329 A1; U.S. Pat. No. 8,529,924 A1; U.S. Pat. No. 7,731,767 A1; U.S. Pat. No. 8,362,125 A1; U.S. Pat. No. 8,652,221; U.S. 2007/0249771 A1; U.S. Pat. No. 6,063,144; U.S. 2013/0178640; U.S. Pat. No. 8,157,873 A1; EP 0457665; U.S. Pat. No. 8,048,290 A1; U.S. Pat. No. 8,053,614 A1; U.S. 2014/0024869 A1; U.S. 2014/0142356 A1; U.S. Pat. No. 9,587,180 A1; U.S. 2014/0171699 A1.

SUMMARY

The present disclosure provides ketone waxes, methods of forming ketone waxes, and compositions comprising ketone waxes.

In at least one embodiment, a ketone wax is provided. The ketone wax includes about 50 wt % or greater $C_{40}$-$C_{90}$ ketone content; about 50 wt % or greater of the ketone wax has a boiling point of 961° F. or greater; and a paraffins content of less than about 10 wt %, as determined by 2-dimensional gas chromatography.

In at least one embodiment, a candle is provided. The candle can include a ketone wax including about 50 wt % or greater $C_{40}$-$C_{90}$ ketone content; about 50 wt % or greater of the ketone wax having a boiling point of 961° F. or greater; and a paraffins content of less than about 10 wt %, as determined by 2-dimensional gas chromatography.

In at least one embodiment, a method for forming a $C_{40}$-$C_{90}$ ketone wax includes exposing a feed stock to a basic catalyst under conditions suitable for coupling carbon chains from the feed to form a composition including a ketone wax, oligomerizing the ketone wax to form a ketone wax having $C_{40}$-$C_{90}$ ketone wax, and distilling and/or extracting the oligomerized ketone wax to provide a $C_{40}$-$C_{90}$ ketone wax of the present disclosure.

DETAILED DESCRIPTION

Figure 1:
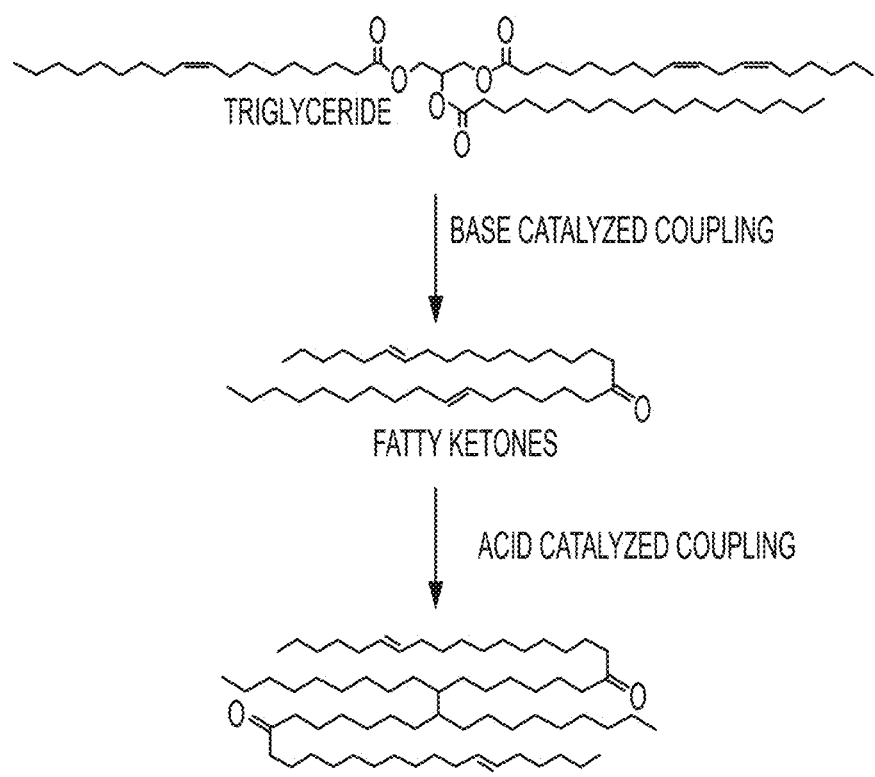
FIG. 1 is a reaction scheme illustrating conversion of triglycerides (i.e., fatty acid derivatives) into oligomerized products, according to one embodiment.

In at least one embodiment, waxes, methods, and compositions are provided. Waxes and compositions of the present disclosure can have various novel properties relative to waxes (and compositions thereof) derived from mineral sources or derived from renewable sources in a conventional manner. Waxes of the present disclosure can be a $C_{40}$-$C_{90}$ ketone wax having: a double bond equivalent value from 1 to 6; less than about 30 wt % (based on the total intensity) of the $C_{40}$-$C_{90}$ ketone wax has a DBE value of 6; about 50 wt % or greater of the $C_{40}$-$C_{90}$ ketone wax composition has a boiling point of 961° F. or greater; has a paraffins content of less than about 10 wt %; a 1R-naphthenes content of from about 0.1 wt % to about 20 wt %; a 2R-naphthenes content of from about 0.1 wt % to about 20 wt %; a 1R-aromatics content of from about 50 wt % to about 99.9 wt %; and/or an oxygen content of from about 1 wt % to about 15 wt %, such as from about 2 wt % to about 10 wt %.

Ketone Waxes

In at least one embodiment, a ketone wax is a $C_{40}$-$C_{90}$ ketone wax. A $C_{40}$-$C_{90}$ ketone wax can include 50 wt % or greater $C_{40}$-$C_{90}$ ketone content, such as about 60 wt % or greater $C_{40}$-$C_{90}$ ketone content, such as about 70 wt % or greater $C_{40}$-$C_{90}$ ketone content, such as about 80 wt % or greater $C_{40}$-$C_{90}$ ketone content, such as about 90 wt % or greater $C_{40}$-$C_{90}$ ketone content, such as about 95 wt % or greater $C_{40}$-$C_{90}$ ketone content, such as about 99 wt % or greater $C_{40}$-$C_{90}$ ketone content, such as about 100 wt %. A $C_{40}$-$C_{90}$ ketone wax can have a double bond equivalent (DBE) value from 1 to about 6, for example 1, 2, 3, 4, 5, or 6. A $C_{40}$-$C_{90}$ ketone wax formed by olefin coupling in the presence of an acidic catalyst, for example, can have a broad distribution of olefins, as represented by double bond equivalents in the oligomer product. DBE values can be obtained by characterizing a product using field desorption time of flight (FD-TOF) mass spectrometry. In particular, the broad distribution of olefins in the resulting oligomer product can be broad within each carbon number represented in the product. For example, for the compounds in the oligomer product, a variety of different double bond equivalent amounts can be present for the compounds corresponding to each carbon number present in the oligomer product.

In at least one embodiment, less than about 30 wt % (based on the total intensity) of the $C_{40}$-$C_{90}$ ketone wax has a DBE value of 6. In at least one embodiment, less than about 20 wt % of the $C_{40}$-$C_{90}$ ketone wax has a DBE value of 5. In at least one embodiment, less than about 20 wt % of the $C_{40}$-$C_{90}$ ketone wax has a DBE value of 4.

In at least one embodiment, about 50 wt % or greater of a C40-C90 ketone wax has a boiling point of 961° F. or greater, such as about 60 wt % or greater, such as about 70 wt % or greater, such as about 80 wt % or greater, such as about 90 wt % or greater, such as about 95 wt % or greater, such as about 99 wt % or greater, such as about 99.9 wt % or greater, such as about 100 wt %.

In at least one embodiment, a $C_{40}$-$C_{90}$ ketone wax has a paraffins content of less than about 10 wt %, such as from about 0 wt % to about 5 wt %, such as from about 0.01 wt % to about 2 wt %, for example 0 wt %, as determined by 2-dimensional gas chromatography. In at least one embodiment, a $C_{40}$-$C_{90}$ ketone wax has a 1R-naphthene equivalent of from about 0.1 wt % to about 20 wt %, such as from about 1 wt % to about 10 wt %, for example about 5 wt %, as determined by 2-dimensional gas chromatography. As used herein, a 1R-naphthene equivalent means a polarity equivalent to a hydrocarbon compound having one saturated ring or one C═C double bond in the molecule. In at least one embodiment, a $C_{40}$-$C_{90}$ ketone wax has a 2R-naphthene equivalent of from about 0.1 wt % to about 20 wt %, such as from about 1 wt % to about 15 wt %, such as from about 5 wt % to about 10 wt %, for example about 8 wt %, as determined by 2-dimensional gas chromatography. As used herein, a 2R-naphthene equivalent means a polarity equivalent to a hydrocarbon compound having two saturated cyclic rings (which can be fused or separated by C—C bonds), one saturated ring plus one C═C double bond, or two C═C double bonds. In at least one embodiment, a $C_{40}$-$C_{90}$ ketone wax has a 1R-aromatic equivalent of from about 50 wt % to about 99.9 wt %, such as from about 70 wt % to about 95 wt %, such as from about 80 wt % to about 90 wt %, for example about 85 wt %, as determined by 2-dimensional gas chromatography. As used herein, a 1R-aromatic equivalent means a polarity equivalent to a hydrocarbon compound having any kind of aromatic ring.

In at least one embodiment, a $C_{40}$-$C_{90}$ ketone wax has an oxygen content of from about 1 wt % to about 15 wt %, such as from about 2 wt % to about 10 wt %, such as from about 4 wt % to about 8 wt %.

In at least one embodiment, a $C_{40}$-$C_{90}$ ketone wax has a kinematic viscosity at 100° C. (Kv100) of at least about 6 cSt or higher, such as at least about 8 cSt, at least about 10 cSt, at least about 12 cSt, at least about 15 cSt, at least about 18 cSt, or at least about 6.0 cSt. Additionally or alternately, a $C_{40}$-$C_{90}$ ketone wax has a kinematic viscosity at 100° C. of about 25 cSt or less, such as about 23 cSt or less, about 21 cSt or less, or about 19 cSt or less. In particular, a $C_{40}$-$C_{90}$ ketone wax has a kinematic viscosity at 100° C. of about 6 cSt to about 23 cSt, or about 8 cSt to about 21 cSt, or about 10 cSt to about 19 cSt. The hardness of the $C_{40}$-$C_{90}$ ketone wax can be characterized based on needle penetration at 25° C. and/or 40° C., e.g., using ASTM D1321. For penetration at 25° C., the $C_{40}$-$C_{90}$ ketone wax can have a hardness value of about 100 or less, or about 80 or less, such as down to about 60 or less.

In at least one embodiment, a $C_{40}$-$C_{90}$ ketone wax has a high melting point relative to the melting point that would be expected for a paraffin wax of similar chain length. For example, a C36 paraffin wax (i.e., a paraffin wax composed of 100% alkanes with 36 carbons in the carbon chain) can have a melting point of about 76° C., while a C35 ketone wax (100% C35 ketones) can have a melting point of about 86° C. A paraffin wax with a melting point of about 86° C. can correspond to a much heavier paraffin wax, such as a $C_{44}$ paraffin wax. It is to be noted that a $C_{40}$-$C_{90}$ paraffin wax can have a substantially greater kinematic viscosity at 100° C. in comparison with a $C_{40}$-$C_{90}$ ketone wax. For commercial applications such as coatings, the combination of low kinematic viscosity ($Kv_{100}$) and high melting point provided by a $C_{40}$-$C_{90}$ ketone wax can provide substantial advantages. ASTM D4419 describes a method for determining transition temperatures (such as melting point) for waxes using differential scanning calorimetry. For melting points described herein, differential scanning calorimetry (DSC) curves can be generated using ASTM method D4419. For melting points described herein, peak melting points can be determined as a peak melting temperature during the heating part of the DSC curve during a second heating cycle of the material, after the heat history of the sample had been erased in the first heating cycle.

More generally, a $C_{40}$-$C_{90}$ ketone wax can be characterized based on a combination of kinematic viscosity at 100° C. and melting point. In at least one embodiment, a $C_{40}$-$C_{90}$ ketone wax can have a kinematic viscosity at 100° C. of about 9 cSt to about 25 cSt and can have a melting point of at least about 50° C. In at least one embodiment, a ketone wax can have a kinematic viscosity ($Kv_{100}$) of about 10 cSt to about 21 cSt and a melting point of at least about 60° C. In at least one embodiment, a ketone wax can have a kinematic viscosity ($Kv_{100}$) of about 11 cSt to about 19 cSt and a melting point of at least about 70° C.

Methods of Making $C_{40}$-$C_{90}$ Ketone Wax

In at least one embodiment, a $C_{40}$-$C_{90}$ ketone wax can be formed by a multistage process (a three stage process) by exposing a feed stock to a basic catalyst under conditions suitable for coupling carbon chains from the feed to form a composition including a ketone wax, oligomerizing the ketone wax to form a ketone wax having $C_{400}$-$C_{90}$ ketone wax, and distilling and/or extracting the oligomerized ketone wax to provide a $C_{40}$-$C_{90}$ ketone wax of the present disclosure.

For the first stage, the catalyst can be effective for converting the fatty acids and/or fatty acid derivatives in the feed into ketones corresponding to a "dimer" of two fatty chains from the feed. Such a coupling reaction can optionally result in production of small molecule(s) containing heteroatoms eliminated during the conversion reaction, such as water, ammonia, carbon monoxide, and/or carbon dioxide. Such small molecules can be separated from the effluent of the coupling reaction in any suitable manner, such as by performing a separation based on boiling point. This initial coupling reaction can be used to make lubricant boiling range compounds, such as ketone waxes, having a carbon chain length of 27 to 39 carbons, advantageously with a relatively narrow distribution of carbon chain lengths. These ketone waxes preferably do not undergo further processing to partially or fully saturated olefin linkages present in the carbon chain and/or to at least partially or fully remove oxygen from the ketone wax. These ketone waxes can have unexpected properties relative to waxes derived from other/conventional sources.

In at least one embodiment, an advantage of forming ketone wax from a renewable feed source can be related to the position of the ketone in the ketone wax. A ketone wax formed from a renewable feed can correspond to ketones formed by coupling of fatty acid (and/or fatty acid derivative) type compounds. The ketones formed from coupling of fatty acid (and/or fatty acid derivative) type compounds with similar chain lengths can tend to have a ketone group located near the center of the compound. This can be in contrast to ketones made by functionalizing a paraffin feed, where the selectivity for forming a ketone near the center of the compound is lower. In at least one embodiment, at least 50 wt % of the ketones in a ketone wax can correspond to ketones with a ketone functional group near the center of the compound, or about 70 wt % or greater, such as 90 wt % or greater, such as up to 100 wt %. In some embodiments, about 50 wt % or greater of the ketones in a ketone wax can correspond to ketones with a ketone functional group on the center carbon atom of the compound, such as about 70 wt % or greater, such as about 90 wt % or greater, such as up to 100 wt %. Having ketones located near the center of the compound (and/or on the center carbon atom of the compound) can potentially be beneficial, for example, for providing a ketone wax with higher crystallinity and/or wax-like properties. This can be due to the (relative) symmetry of ketones with a ketone functional group at or near the central carbon atom in a compound.

A ketone functional group can be considered as near the center of the ketone when the ketone functional group is located on a carbon atom within 5 carbon atoms of the center of the ketone compound. The center of a ketone compound can be determined based on the chain length of the ketone according to IUPAC naming rules. The center of a carbon chain can be defined by adding one to the chain length according to IUPAC naming rules and then dividing by two, with the resulting number corresponding to the center carbon atom. As an example, for a carbon chain length of 25, the center carbon atom can correspond to the thirteenth carbon atom from an end of the chain (i.e., [25+1]/2=13). For a carbon chain with an even number of carbon atoms according to IUPAC naming rules, adding one to the chain length and then dividing by two can result in a fractional number. The two carbon atoms corresponding to rounding up and rounding down of the fractional number can both be considered center carbon atoms.

Although the distribution of carbon chain lengths can be narrow, the ketone wax described herein can have a distribution of carbon chain lengths due to the nature of how the compositions are made. For the compounds in a ketone wax having a carbon chain length of 27 carbons to 39 carbons, the compounds can include at least three different chain lengths in substantial amounts. For example, the compounds having a carbon chain length of 27 carbons to 39 carbons can include at least 15 wt % (or at least 20 wt %) of compounds having a first carbon chain length, at least 15 wt % (or at least 20 wt %) of compounds having a second carbon chain length, and at least 15 wt % (or at least 20 wt %) of compounds having a third carbon chain length. Optionally, the largest difference in carbon chain length between any two of the first carbon chain length, the second carbon chain length, and the third carbon chain length can be 6 carbons or less, or 4 carbons or less.

The ketone wax formed by the first stage described herein can include compounds with carbon chain lengths of 27 carbons to 39 carbons, or 30 carbons to 39 carbons. In at least one embodiment, the ketone wax formed by the first stage can include at least 80 wt %, or at least 90 wt %, or at least 95 wt % (such as up to 10) wt %) of compounds having a carbon chain length of 27 carbons to 39 carbons, or 30 carbons to 39 carbons. The ketone wax formed by the first stage can also include a ketone functional group for at least a portion of the compounds having a carbon chain length of 27 carbons to 39 carbons (or 30 carbons to 39 carbons). The ketone wax formed by the first stage can substantially correspond to ketone compounds, with at least about 80 wt % of the compounds having 27 carbons to 39 carbons (or 30 carbons to 39 carbons) in the ketone wax corresponding to ketones, or at least about 90 wt %, or at least about 95 wt %, such as up to about 100 wt %. In at least one embodiment, the ketone wax formed by the first stage can include a sufficient number of oxygenates (such as ketones) to provide properties different than those of a conventional wax product. For example, about 30 wt % to about 100 wt % of the compounds having 27 carbons to 39 carbons (or 30 carbons to 39 carbons) can correspond to oxygenates (such as ketones), or about 40 wt % to about 90 wt %, or about 50 wt % to about 80 wt %.

In at least one embodiment, the distribution of carbon chain lengths in the ketone wax formed by the first stage having 27 carbons to 39 carbons (or 30 carbons to 39 carbons) can be relatively narrow. In such aspects, a substantial portion of the carbon chain lengths can correspond to ketone waxes that differ in chain length by 6 carbons or less, or 4 carbons or less. As an example, a ketone wax formed by the first stage including compounds having a chain length of 31 carbons, 33 carbons, and 35 carbons can correspond to a composition with compounds that differ by 4 carbons or less. In such aspects, at least 80 wt % of the compounds having 27 carbons to 39 carbons (or 30 carbons to 39 carbons) can have chain lengths that differ by about 6 carbons or less, or about 4 carbons or less, or at least 90 wt %, or at least 95 wt %.

Additionally or alternatively, ketone waxes formed by the first stage having 27 carbons to 39 carbons (or 30 carbons to 39 carbons) can have varying degrees of unsaturation. Because the ketone wax is not hydroprocessed, the ketone wax formed by the first stage retains a substantial portion of olefinic bonds/compounds. For example, the ketone wax formed by the first stage can include at least about 20 wt % of olefins, such as at least about 30 wt %, at least about 40 wt %, at least about 50 wt %, at least about 60 wt %, or at least about 70 wt %. Additionally or alternatively, the ketone wax formed by the first stage can include about 100 wt % olefinic compounds or less, such as about 90 wt % or less, about 80 wt % or less, about 70 wt % or less, about 60 wt % or less, or about 50 wt % or less. In particular, about 20 wt % to about 100 wt % of the compounds having 27 carbons to 39 carbons (or 30 carbons to 39 carbons) can correspond to olefinic compounds, or about 30 wt % to about 90 wt %, or about 40 wt % to about 70 wt %.

A ketone wax formed by the first stage as described herein can have a combination of properties that can be beneficial in various types of end product applications. For example, for a ketone wax formed by the first stage having a specified viscosity, the hardness of a ketone wax can be comparable to the hardness for a conventional paraffin wax having a similar viscosity. However, the melt point of such a ketone wax can be substantially higher than the corresponding paraffin wax having a similar viscosity. This can allow ketone wax to be valuable for use in hot melt adhesive applications.

In at least one embodiment, a ketone wax formed by the first stage can have a kinematic viscosity at 100° C. of at least about 3.0 cSt, such as at least about 3.5 cSt, at least about 4.0 cSt, at least about 4.5 cSt, at least about 5.0 cSt, at least about 5.5 cSt, or at least about 6.0 cSt. Additionally or alternatively, a ketone wax formed by the first stage can have a kinematic viscosity ($Kv_{100}$) of about 7.5 cSt or less, such as about 7.0 cSt or less, about 6.5 cSt or less, or about 6.0 cSt or less. In particular, a ketone wax formed by the first stage can have a kinematic viscosity ($Kv_{100}$) at 100° C. of about 3.0 cSt to about 7.5 cSt, or about 3.0 cSt to about 6.5 cSt, or about 4.0 cSt to about 7.5 cSt. The hardness of the ketone wax can be characterized based on needle penetration at 25° C. and/or 40° C., e.g., using ASTM D1321. For penetration at 25° C. the ketone wax formed by the first stage can have a hardness value of about 6.0 or less, or about 5.5 or less, such as down to about 4.0. For penetration at 40° C., the ketone wax formed by the first stage can have a hardness value of about 8.0 or less, or about 7.5 or less, such as down to about 5.0.

In at least one embodiment, a ketone wax formed by the first stage can have a high melting point relative to the melting point that would be expected for a paraffin wax of similar chain length. For example, a C36 paraffin wax (i.e., a paraffin wax composed of 100% alkanes with 36 carbons in the carbon chain) can have a melting point of about 76° C., while a C35 ketone wax (100% C35 ketones) can have a melting point of about 86° C. A paraffin wax with a melting point of about 86° C. can correspond to a much heavier paraffin wax, such as a C44 paraffin wax. However, a C44 paraffin wax can have a substantially greater kinematic viscosity at 100° C. in comparison with a C35 ketone wax. The kinematic viscosity ($Kv_{100}$) of a C44 paraffin wax can be at least about 11 cSt, while the kinematic viscosity of a C35 ketone wax can be about 6.0 cSt. For commercial applications such as free standing candles, the combination of low kinematic viscosity ($Kv_{100}$) and high melting point provided by a ketone wax formed by the first stage can provide substantial advantages. ASTM D4419 describes a method for determining transition temperatures (such as melting point) for waxes using differential scanning calorimetry. For melting points described herein, DSC curves were generated using a method similar to ASTM D4419. For melting points described herein, peak melting points can be determined as a peak melting temperature during the heating part of the DSC curve during a second heating cycle of the material, after the heat history of the sample had been erased in the first heating cycle.

More generally, a ketone wax formed by the first stage can be characterized based on a combination of kinematic viscosity at 100° C. and melting point. In at least one embodiment, a ketone wax formed by the first stage can have a kinematic viscosity at 100° C. of about 6.0 cSt to about 7.5 cSt and can have a melting point of at least about 83° C. In at least one embodiment, a ketone wax can have a kinematic viscosity ($Kv_{100}$) of about 3.0 cSt to about 7.5 cSt and a melting point of at least about 78° C. In at least one embodiment, a ketone wax can have a kinematic viscosity ($Kv_{100}$) of about 3.0 cSt to about 6.5 cSt and a melting point of at least about 78° C.

An initial step in forming a ketone wax (or other long chain ketone) can be to perform a coupling reaction to convert two shorter carbon chains (such as fatty acids) into a ketone having a longer carbon chain. A catalyst suitable for facilitating a coupling or conversion reaction to form ketones from carboxylic acids and/or carboxylic acid derivatives (such as amides, including substituted amides, or glycerides, including triglycerides) can comprise or be a catalyst including a rare earth metal, such as a metal salt of a rare earth metal, an alkali metal, an alkaline earth metal, or a combination thereof. Some suitable catalysts can include clay materials containing a rare earth metal, an alkali metal, and/or an alkaline earth metal. For example, hydrotalcite is a clay including magnesium hydroxide. Additionally or alternately, some examples of suitable catalysts can include support materials impregnated with a rare earth metal salt, an alkali metal salt, and/or an alkaline earth metal salt, such as an oxide, hydroxide, or carbonate. For example, a refractory support such as titanium oxide, zirconium oxide, and/or cerium oxide can be impregnated with a lanthanum, sodium, and/or potassium salt, such as potassium carbonate. Additionally or alternately, some examples of suitable catalysts can include bulk and/or supported versions of rare earth, alkali, or alkaline earth metal salts, such as magnesium oxide and/or cesium oxide. More generally, alkali metal salts can include salts of Na, K, Rb, and/or Cs, while alkaline earth metal salts can include salts of Mg, Ca, Sr, and/or Ba. Rare earth metal salts can include, but are not limited to, salts of La, Ce, Nd, and/or Y. Thus, a reference herein to a rare earth metal or rare earth metal salt is defined to include at least La, Ce, Nd, and/or Y.

A suitable catalyst can include at least about 5 wt % of a rare earth metal salt, alkali metal salt, or alkaline earth metal salt relative to the total catalyst weight, or at least about 15 wt %, or at least about 25 wt %, such as up to 75 wt % or more. For catalysts based on clays, the catalyst can include about 75 wt % or less of rare earth metal salt, alkali metal salt, or alkaline earth metal salt, or about 50 wt % or less, or about 35 wt % or less, or about 25 wt % or less, such as down to about 15 wt % or less. For supported catalysts, the catalyst can include about 35 wt % or less of rare earth metal salt, alkali metal salt, or alkaline earth metal salt, or about 25 wt % or less, or about 15 wt % or less, such as down to about 5 wt % or less. In general, higher percentages of a rare earth metal salt, an alkali metal salt, or an alkaline earth metal salt can be desirable, but practical factors may limit the amount of rare earth metal salt, alkali metal salt, and/or alkaline earth metal salt. For example, supported catalysts may be limited based on the amount of salt that can be impregnated or otherwise added to a support in a manner stable in the reaction environment. Similarly, the amount of rare earth metal salt, alkali metal salt or alkaline earth metal salt present in a clay may be limited in order to form a stable clay.

Some catalysts suitable for catalyzing a coupling reaction can also be suitable for converting amides to cyanide groups via an alternative reaction pathway. For feeds including fatty amides as part of the fatty acid derivatives in the feed, a coupling catalyst including oxides of Mg, Ca, or Al can also potentially convert at least a portion of amides to cyanide groups as a competing reaction to coupling the amides to form ketones. It is noted that Mg, Ca, or Al oxides may be present as a support material for a coupling catalyst.

To convert fatty acids and/or fatty acid derivatives to ketones, a suitable feedstock can be exposed to a catalyst containing a rare earth metal, alkali metal, and/or alkaline earth metal under effective conditions for performing the conversion reaction via a condensation reaction. The effective conditions for the conversion reaction can advantageously include a temperature from about 300° C. to about 450° C. Hydrogen gas is optionally used to facilitate the condensation reaction so that ketone wax products are not deoxygenated. As a result, in such embodiments, a hydrogen partial pressure of about 1.8 MPag to about 35 MPag can be present. In such a configuration, the reaction temperature can be from about 300° C. to about 450° C. or about 320° C. to about 360° C., in order to balance the benefits of the reactions occurring in the single reaction environment.

Exposure of (free) fatty acids and/or fatty acid derivatives (such as glycerides or amides) to a rare earth, alkali metal, and/or alkaline earth metal catalyst can tend to generate a mixture of products. One of the majority products in such a mixture can generally be a fatty ketone. It is believed that fatty ketones are formed via a reaction between carbon chains of two fatty amide, fatty acid, or fatty acid derivative molecules. By using a feed having fatty carbon chains of about 14 to about 22 carbons in length, a resulting ketone wax product can be formed having a carbon chain length of 27 to 39 carbons in length. Additionally or alternately, this ketone wax product can have properties relative to traditional waxes and/or other hydrocarbon-like mixtures having a similar average carbon chain length.

In addition to the coupling reaction described above to form ketone waxes, a second stage includes oligomerization (such as additional dimerization or trimerization) of the ketone wax formed by the first stage is performed to form still heavier oligomerized compounds including $C_{40}$-$C_{90}$ ketone waxes.

FIG. 1 is a reaction scheme illustrating conversion of triglycerides (i.e., fatty acid derivatives) into oligomerized products. In FIG. 1, a triglyceride is shown as an initial starting molecule. Base catalyzed coupling (the first stage) can be used to convert the triglycerides into fatty ketones, where the length of the ketone carbon chain can roughly correspond to the combined length of the two glyceride chains coupled to form the ketone. In the example shown in FIG. 1, the triglyceride can correspond to a triglyceride including one or more olefins in the fatty acid carbon chain, so that the resulting ketone can correspond to an olefinic ketone. The olefinic ketone can then be coupled under acidic coupling conditions (the second stage) to form an oligomerized product such as a ketone wax having a $C_{40}$-$C_{90}$ ketone wax content. In the example shown in FIG. 1, the oligomerized product can correspond to acidic coupling of two olefinic ketones. Depending on the nature of the reaction conditions and available feed, other acidic coupling reactions can lead to formation of products based on coupling of an olefinic ketone with a glyceride chain, or based on coupling of two glycerides. For molecules other than glycerides, such as fatty amides, free fatty acids, or other fatty acid derivatives, a reaction mechanism analogous to the reaction shown in FIG. 1 can lead to formation of ketones and/or oligomerized products.

In aspects involving a feed that contains glycerides such as triglycerides, the rare earth, alkali, and/or alkaline earth catalysts of the present disclosure can allow for the direct conversion of triglycerides and other glycerides to fatty ketones, without requiring an initial step to form the free fatty acid. The addition of hydrogen and/or water to generate free fatty acids may also not be required. Instead, exposing a glyceride-containing feedstock to the rare earth, alkali, and/or alkaline earth metal can allow for direct conversion of glycerides to mixtures of ketones.

To form the heavier oligomerized compounds including $C_{40}$-$C_{90}$ ketone waxes, a ketone wax formed by the first stage as described above can, in the second stage, be exposed to conditions suitable for further oligomerization based on coupling of olefin linkages in the fatty acid carbon chains in the presence of an acidic catalyst. This can result in formation of larger oligomers. These larger oligomers are not hydroprocessed. In at least one embodiment, the further oligomerization in the presence of an acidic catalyst (the second stage) can occur in the same reaction environment as the coupling in the presence of a basic catalyst (the first stage) (e.g., the first stage and second stage are performed concurrently), or the oligomerization in the presence of an acidic catalyst (the second stage) can occur prior to coupling in the presence of a basic catalyst (the first stage).

The acid catalyzed coupling reaction of the second stage can be carried out at suitable temperatures, for example about 150° C. to about 400° C., about 200° C. to about 400° C., or about 250° C. to about 350° C. A liquid hourly space velocity of from about 0.1 to about 10 v/v/h, particularly about 0.5 to about 5 v/v/h, can be applied. Hydrogen gas is optionally present. As a result, a hydrogen partial pressure of about 1.8 MPag to about 35 MPag can be present in at least one embodiment. The presence of hydrogen can reduce cyclic oligomer formation.

The resulting oligomers formed by olefin coupling in the presence of an acidic catalyst can have a broad distribution of olefins, as represented by double bond equivalents (DBEs) in the oligomer product. DBE values can be obtained by characterizing a product using field desorption time of flight (FD-TOF) mass spectrometry. In particular, the broad distribution of olefins in the resulting oligomer product can be broad within each carbon number represented in the product. For example, for the compounds in the oligomer product, a variety of different double bond equivalent amounts can be present for the compounds corresponding to each carbon number present in the oligomer product.

In aspects where sequential processing is used to form oligomers from the ketone wax of the first stage, the DBE values of the oligomers formed by the second stage can be characterized for compounds with carbon numbers larger than 20. For such compounds, the percentage of compounds with a DBE value of 6 can be 30% or less of the total intensity detected using FD-TOF for each carbon chain length. Additionally or alternately, the percentage of compounds with a DBE value of 5 can be 20% or less of the total intensity for each carbon chain length. Additionally or alternately, the percentage of molecules with a DBE value of 4 can be 20% or less of the total intensity for each carbon chain length.

In aspects where both an acidic and a basic catalyst are present in the same environment, so that oligomerized ketones can be formed in a single processing step, the DBE values can be characterized for compounds with carbon numbers larger than 20. For such compounds, the percentage of molecules with a DBE value of 6 can be 45% or less of the total intensity detected using FD-TOF for a given carbon chain length. Additionally or alternately, the percentage of molecules with a DBE value of 5 can be 20% or less of the total intensity for a given carbon number. Additionally or alternately, the percentage of molecules with a DBE value of 4 can be 20% or less of the total intensity for a given carbon number.

In a third stage, the mixture of oligomerized compounds can be distilled to produce a $C_{40}$-$C_{90}$ ketone wax of the present disclosure.

Basic Catalysts

Catalysts having sufficient acidic or basic properties to be effective in coupling fatty acids, fatty acid esters, fatty alcohols, fatty olefins, or glycerides (mono-, di-, or tri-glycerides) can be identified by determining the molar ratio of chemisorption of $CO_2$ and $NH_3$ over these materials. $CO_2$, a weak acid, can be used to titrate the basic sites present on the catalysts. Likewise, $NH_3$, a strong base, can be titrated to indicate the acidic sites on these materials. Many factors can determine the actual amount of chemisorption, such as surface area of the material (which can be affected by the catalyst preparation method), the measurement temperature for chemisorption, and the testing pressure for chemisorption. The ratio of adsorbed $CO_2$ and $NH_3$ can indicate a relative acidity or basicity.

A "basic" catalyst can be a material having a molar ratio of chemisorption of $CO_2$ per gram of material to the chemisorption of $NH_3$ per gram of material greater than about 0.5, or greater than about 0.75, or greater than about 1.0, when tested as described below. In non-limiting examples, the "carbon dioxide/ammonia ratio" can range from about 1.0 to about 100, particularly from about 1.0 to about 50 or from about 1.0 to about 40.

An "acidic" catalyst can be a catalyst having a carbon dioxide/ammonia ratio of less than about 0.5, or less than about 0.3, or less than about 0.2, when tested as described below. In various embodiments, the values can range from about 0.05 to about 0.5, particularly from about 0.05 to about 0.3 or from about 0.05 to about 0.2.

Determination of carbon dioxide/ammonia ratio (i.e. the molar ratio of chemisorption of $CO_2$ per gram of catalyst to the chemisorption of $NH_3$ per gram of catalyst) can be conducted using a Mettler™ TGA/SDTA 851 thermogravimetric analysis system at ambient pressure. The catalyst sample can be calcined in flowing air at ~500° C. for three hours or at least until a constant sample weight is obtained. The temperature of the sample can then be reduced in flowing air (helium can also be used) to the desired temperature of chemisorption. Next, the sample can be allowed to equilibrate at the desired temperature in flowing helium and weighed. Chemisorption of carbon dioxide can be measured at ~150° C., and chemisorption of ammonia can be measured at ~250° C. After being weighed, the sample can be subjected to a number of pulses (~12 seconds/pulse) of gaseous mixture containing helium and either carbon dioxide or ammonia until a constant weight can be obtained. The gas mixture can contain ~10 mol % carbon dioxide or ammonia, with the remainder being helium. After each pulse of the gas mixture being tested, the sample can be flushed with flowing helium for ~3 minutes. About 20 separate pulses of the gas mixture can be used in each test. The increase in weight of the sample in terms of mg/g material based on the sample weight after calcination can be used to determine the moles of $C_{O2}$ or $NH_3$ adsorbed per gram of material.

Molar ratios of chemisorption of $CO_2$ to the chemisorption of $NH_3$ per gram of material for some representative catalysts are shown in Table 1.

TABLE 1

| Materials | $CO_2/NH_3$ Chemisorption Molar Ratio |
|---|---|
| MgO (Elastomag ™ 170) | ~7.82 |
| MgO (MagChem ™ 200AD) | ~6.92 |
| γ-$Al_2O_3$ (Alfa ™ # 43832) | ~0.47 |
| Hydrotalcite (Pural ™ MG30) | ~1.35 |
| Hydrotalcite (Pural ™ MG63) | ~1.95 |
| Hydrotalcite (Pural ™ MG70) | ~2.30 |
| W/$ZrO_2$ | ~0.07 |
| $La_2O_3$ | ~6.64 |

TABLE 1-continued

| Materials | $CO_2/NH_3$ Chemisorption Molar Ratio |
|---|---|
| La/SiO$_2$ | ~0.92 |
| AlPO$_x$ | ~0.75 |
| NdAlPO$_x$ | ~1.04 |
| YAlPO$_x$ | ~0.86 |
| PrAlPO$_x$ | ~1.05 |
| La/ZrO$_2$ (~700° C. calcined) | ~1.06 |
| Y$_2$O$_3$—~5% ZrO$_2$ | ~6.17 |
| Y$_2$O$_3$—~25% ZrO$_2$ | ~1.18 |
| Nd$_2$O$_3$ | ~35.37 |
| Sm$_2$O$_3$ | ~15.61 |
| Y$_2$O$_3$ | ~14.95 |
| CeO$_2$ | ~8.48 |
| Pr$_2$O$_3$ | ~1.56 |
| TiO$_2$ | ~0.55 |
| ZrO$_2$ | ~0.33 |
| SAPO-34 | ~0.19 |
| ZSM-5 | ~0.16 |
| SiO$_2$ | ~0.02 |
| USY | ~0.00 |
| ~75/~25 SiO$_2$/Al$_2$O$_3$ | ~0.38 |
| ~50/~50 SiO$_2$/Al$_2$O$_3$ | ~0.47 |
| 25/25 SiO$_2$/Al$_2$O$_3$ | ~0.41 |
| 13/87 SiO$_2$/Al$_2$O$_3$ | ~0.42 |
| La$_2$O$_3$/SiO$_2$ | ~0.92 |
| MCM-41 | ~0.44 |

Catalysts suitable for coupling fatty acids, fatty amides, fatty acid esters, fatty alcohols, fatty olefins, glycerides (mono-, di-, or tri-glycerides), or other fatty acid derivatives can be oxides and mixed oxides of metals of Group 1 to Group 6, Group 12 to Group 15, Lanthanide Series, or Actinide Series of the Periodic Table of Elements. The catalysts can also comprise acidic or basic clays such as hydrotalcites, bentonite, montmorillonite, aluminosilicates such as zeolites, aluminophosphates, or metalloaluminophosphates (where metal comprises or is, for example, Si, Nd, Y, Pr, Ce, Ti, or Zr).

In at least one embodiment, the coupling catalysts can comprise two or more metal oxides, particularly one Group 4 metal oxide and one or more selected from Group 2, Group 3, Lanthanide Series, and Actinide Series metal oxides. In at least one embodiment, the coupling catalysts can be selected from oxides of Group 2, Group 12, or Group 13 elements, and mixtures thereof. In at least one embodiment, the coupling catalysts can be either naturally occurring or synthetic clays such as hydrotalcite, bentonite, montmorillonite, or mixtures thereof. Compositions for each individual component in the oxide mixtures can vary from about 1 wt % to about 99 wt %. The oxides can be prepared using a variety of methods, although generally they are prepared by converting a suitable precursor by precipitation from solution and/or calcination. Suitable precursors can include metal salts, such as halides, sulfates, phosphates, halides, nitrates, hydroxides, oxychlorides, alkoxides, and acetates.

In some embodiments, a metal oxide useful as a catalyst can be produced by first preparing a liquid solution comprising a salt of the metal in a solvent, such as water. The resultant solution can then be subjected to conditions sufficient to cause precipitation of the solid oxide material, such as by the addition of a precipitating reagent, typically a base such as sodium hydroxide or ammonium hydroxide. The liquid solution can be generally maintained at a temperature at or below 200° C. during the precipitation, for example in the range of from 0° C. to 200° C., such as from 20° C. to 100° C. In an embodiment, the resulting gel can be hydrothermally treated at a temperature of at least 80° C., particularly at least 100° C., for up to 10 days, such as up to 5 days, for example up to 3 days. The resulting material can then be recovered, for example by filtration or centrifugation, washed, and dried. The resulting particulate material typically can then be calcined, normally in an oxidizing atmosphere, at a temperature of at least 400° C., such as from 400° C. to 800° C., for up to 48 hours, such as for 0.5 hours to 24 hours, for example for 1 hour to 10 hours.

When two or more metal oxides are used for the coupling of fatty acids, fatty acid esters, fatty alcohols, fatty olefins, or glycerides (mono-, di-, or tri-glycerides), they may either be co-precipitated or precipitated separately and combined with each other at any later stage of processing including as calcined solid particles.

Acidic Catalysts

In addition to or as an alternative to coupling in the presence of a basic catalyst as described above, fatty acid and/or fatty acid derivative coupling can be catalyzed by a catalyst component having adequate acidity to catalyze the conversion chemistry. According to the definitions used herein, acidic catalysts can correspond to a class of materials with the "carbon dioxide/ammonia ratio" in the range of 0.05 to 0.5, particularly from 0.05 to 0.3 or from 0.05 to 0.2.

Although acidic catalysts can perform other functions, acidic catalysts can be suitable for catalyzing the reaction of unsaturated fatty acids to make dimers and higher oligomers of fatty acids. For this reason, the acidic catalysts can be referred to as oligomerization catalysts. Oligomerization reactions can be carried out with suitable catalysts at high temperature. Suitable catalysts can include molecular sieves (both aluminosilicate zeolites and silicoaluminophosphates), metalloaluminophosphates, amorphous aluminosilicates, cationic acidic clays, and other solid acid catalysts or mixtures thereof. Examples of acid catalysts can include but are not limited to large pore zeolites (e.g., Faujasite, Beta, MWW family, etc.), medium (10-ring) to small (8-ring) pore zeolites (e.g., MFI, CHA, MOR, etc.) with small particle sizes, acidic mixed metal oxides (WO$_x$/ZrO$_2$, MoO$_x$/ZrO$_2$), alumina, silica-alumina, and acidic clays, or mixtures thereof.

Examples of the molecular sieves include the large (>12-ring pore opening), medium (10-ring opening) or small (<8-ring pore opening) pore type. The molecular sieves structure types can be defined using three letter codes. Non-limiting examples of small pore molecular sieves can include AEI, AFT, ANA, APC, ATN, ATT, ATV, AWW, BIK, CAS, CHA, CHI, DAC, DDR, EDI, ERI, GIS, GOO, KFI, LEV, LOV, LTA, MER, MON, PAU, PHI, RHO, ROG, SOD, THO, and substituted forms thereof. Non-limiting examples of medium pore molecular sieves can include AFO, AEL, EUO, HEU, FER, MEL, MFI, MTW, MTT, MWW, TON, and substituted forms thereof. Non-limiting examples of large pore molecular sieves can include BEA, CFI, CLO, DNO, EMT, FAU, LTL, MOR and substituted forms thereof. In one embodiment, zeolite catalysts can have a Si/Al molar ratio of greater than 2 and at least one dimension of the pore openings greater than or equal to 10-ring. Solid zeolites for some embodiments can include ZSM-5 (MFI), zeolite beta (BEA), USY family zeolites (FAU), MCM-22, MCM-49, and MCM-56 (MWW). Mesoporous materials with pore openings greater than 20 angstroms, such as the MCM-41 family and SBA-15 type with aluminum incorporated into the structure and thus possessing acidity, can also be used as oligomerization catalysts.

An additional or alternative class of acidic materials can include metalloaluminophosphates (MeAPO), where the metal (Me) can comprise silicon, transition metal elements such as Ti, Zr, Fe, Co, Ni, Cu and Zn, and/or rare-earth elements such as Y, La, Ce, Pr, Nd, Sm and Gd. Acidic clays can include acidic, natural or synthetic montmorillonites, bentonite, silica clay, alumina clay, magnesia clay, and silica-alumina clay. Commercially available acidic forms of Filtrol™ clays can also be suitable.

Other solid acid catalysts, such as acidic mixed metal oxides $WO_3/ZrO_2$ and $MoO_3ZrO_2$, other metal oxides such as sulfated zirconia, $SiO_2/ZrO_2$, $Al_2O_3/ZrO_2$, $MgO/SiO_2$, and Nafions™ or other acidic ion-exchanged resins such as Dowex™ and Amberlyst™ cation exchanged resin can also be suitable for the oligomerization reaction.

Fatty Acid (Derivative) Feeds

Regardless of the initial source, feeds usable in the present disclosure can include any of those which comprise (free) fatty acids, fatty acid derivatives (such as fatty amides, including substituted fatty amides), or glycerides (another type of fatty acid derivative) such as triglycerides, diglycerides, monoglycerides. The fatty acids and/or fatty acid derivatives typically contain aliphatic hydrocarbon chains in their structure having from 8 to 36 carbons, for example from 10 to 26 carbons or from 14 to 22 carbons. The fatty acid/acid derivative constituents in a feed can be determined, for example, by using Gas Chromatography (GC) analysis and/or liquid chromatography-mass spectrometry (LCMS) analysis. In at least one embodiment, a majority (i.e., greater than 50%) of the fatty amide/acid/acid derivatives can correspond to molecules with carbon chain lengths of $C_{14}$ to $C_{22}$.

In at least one embodiment, the production of ketones and/or oligomerized products can be based on processing of fatty acids, glycerides (such as monoacylglycerides, diacylglycerides, and/or triacylglycerides), and/or other fatty acid derivatives within a feed. With regard to the content of fatty acids and fatty acid derivatives (including glycerides and fatty amides) in a feedstock, the feedstock can include at least about 10 wt % of fatty acids/acid derivatives, for example at least about 25 wt %, particularly at least about 40 wt %, at least about 60 wt %, or at least about 80 wt %. Additionally or alternatively, the feed can be composed entirely of fatty acids/acid derivatives, or the fatty acids/acid derivative content of the feed can be about 99 wt % or less, for example about 95 wt % or less, about 90 wt % or less, about 75 wt % or less, or about 50 wt % or less.

Feedstocks

In at least one embodiment, a feed containing amides, acids, or acid derivatives will be available from an external source. In other aspects, a suitable feed can be derived from biomass from a suitable biological source.

A feed derived from a biological source (i.e., a biocomponent feed(stock)) includes a feedstock derived from a biological raw material component, such as vegetable fats/oils or animal fats/oils, fish oils, pyrolysis oils, and algae lipids/oils, as well as components of such materials, and in some embodiments can specifically include one or more types of lipid compounds. Lipid compounds are typically biological compounds that are insoluble in water, but soluble in nonpolar (or fat) solvents. Non-limiting examples of such solvents include alcohols, ethers, chloroform, alkyl acetates, benzene, and combinations thereof.

Major classes of lipids can include fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Examples of vegetable oils include, but are not limited to, rapeseed (canola) oil, soybean oil, coconut oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, tallow oil, rice bran oil, and the like, and combinations thereof.

Vegetable oils as referred to herein can also include processed vegetable oil material as a portion of the feedstock. Non-limiting examples of processed vegetable oil material include fatty acids and/or fatty acid alkyl esters. Alkyl esters can typically include $C_1$-$C_5$ alkyl esters. One or more of methyl, ethyl, and propyl esters can be preferred.

Examples of animal fats that can be used in accordance with the present disclosure include beef fat (tallow), hog fat (lard), turkey fat, fish fat/oil, chicken fat, and the like, and combinations thereof. The animal fats can be obtained from any suitable source including restaurants and meat production facilities.

Animal fats as referred to herein also include processed animal fat material. Non-limiting examples of processed animal fat material include fatty acids and/or fatty acid alkyl esters. Alkyl esters can typically include $C_1$-$C_5$ alkyl esters. One or more of methyl, ethyl, and propyl esters can be preferred.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt %, of lipids based on total weight of the biomass itself.

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysts carterae, Prymnesium parvum. Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryacoccus, Bracteococcus, Chaetoceros, Carteria, Chlamdomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cmanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcvstis, Myxosarcina, Nodularia, Nostoc, Nostochopsis, Oscillatoria, Phormidiumn, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

Other feeds usable in the present disclosure can include those comprising primarily triglycerides and free fatty acids (FFAs). The triglycerides and FFAs typically contain aliphatic hydrocarbon chains in their structure having from 8 to 36 carbons, particularly from 10 to 26 carbons, for example from 14 to 22 carbons. Types of triglycerides can be determined according to their fatty acid constituents. The fatty acid constituents can be readily determined using Gas Chromatography (GC) analysis. This analysis involves extracting the fat or oil, saponifying (hydrolyzing) the fat or oil, preparing an alkyl (e.g., methyl) ester of the saponified fat or oil, and determining the type of (methyl) ester using GC analysis. In one embodiment, a majority (i.e., greater than 50%) of the triglyceride present in the lipid material is made of $C_{10}$ to $C_{26}$ fatty acid constituents, based on total triglyceride present in the lipid material. Further, a triglyceride is a molecule having a structure identical to the reaction product of glycerol and three fatty acids. Thus, although a triglyceride is described herein as being comprised of fatty acids, it should be understood that the fatty acid component does not necessarily contain a carboxylic acid hydrogen. If triglycerides are present, a majority of triglycerides present in the feed can particularly be comprised of $C_{12}$ to $C_{22}$ fatty acid constituents, based on total triglyceride content. Other types of feed that are derived from biological raw material components can include fatty acid esters, such as fatty acid alkyl esters (e.g., FAME and/or FAEE).

Stage Three—Further Processing of Ketone-Containing Product or Oligomerized Product After forming a ketone wax product and/or oligomer product according to the methods above, the ketone wax/oligomer product can be distilled or extracted to form a ketone wax having 50 wt % or greater $C_{40}$-$C_{90}$ ketone wax.

In at least one embodiment, a first reactor can contain the acidic and/or basic catalyst (for dimerization-oligomerization). The effluent from the first reactor can then be passed into one or more gas-liquid separators. A feed for processing can first be exposed to one or more catalyst beds containing acidic and/or basic catalysts (for dimerization/oligomerization).

A gas-liquid separation can then be performed using a separator tray or another type of reactor internal for performing a gas-liquid separation. The liquid portion of the effluent from the first catalyst bed(s) can then be exposed to the second catalyst bed(s).

In at least one embodiment, the acidic and/or basic catalyst can be configured as stacked beds. For example, in this type of configuration, a reactor or reaction system can contain one or more initial beds of a basic catalyst for converting triglycerides and/or other fatty acids and/or fatty acid derivatives to ketones. As described above, exposing a glyceride-containing feed to the one or more initial beds of basic catalyst can result in production of an effluent containing ketones based on the carbon chains in the glycerides.

Figure 2:
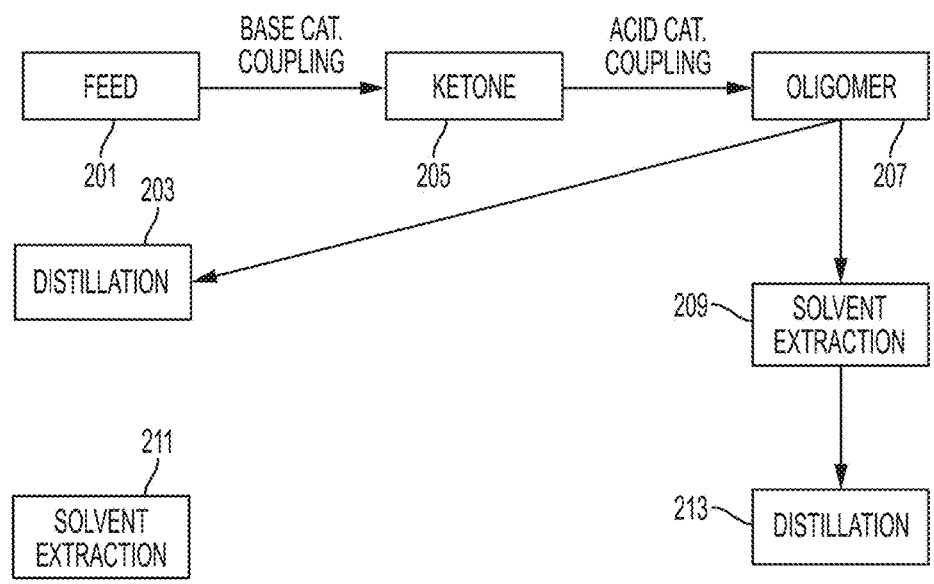
FIG. 2 is a method for manufacturing C40-C90 ketone waxes of the present disclosure, according to one embodiment.

FIG. 2 is a method for manufacturing $C_{40}$-$C_{90}$ ketone waxes of the present disclosure. In FIG. 2, a feed 201 can include fatty acids and/or fatty acid derivatives. The feed 201 can be exposed to a basic catalyst under coupling conditions to form a coupled effluent 205 including a ketone wax product. Coupled effluent 205 can then be exposed to an acidic catalyst under coupling to conditions to form an oligomerized product 207 having $C_{40}$-$C_{90}$ ketone wax. The oligomerized product 207 can then be introduced into a distillation column to provide a $C_{40}$-$C_{90}$ ketone wax 203 of the present disclosure. Ketone wax 203 can then be solvent extracted to provide another $C_{40}$-$C_{90}$ ketone wax 211 of the present disclosure. Alternatively, the oligomerized product 207 can be solvent extracted to produce a purified $C_{40}$-$C_{90}$ ketone wax 209 of the present disclosure. Ketone wax 209 can then be solvent extracted to produce another $C_{40}$-$C_{90}$ ketone wax 213 of the present disclosure.

Distillation can be performed in a distillation tower. A distillation tower typically has one or more reboilers disposed beneath it. Reboilers are heat exchangers typically used to provide heat to the bottom of industrial distillation columns. During use, a fractional distillation tower separates light products (such as $C_{32}$ or lower ketones) from heavier products (such as $C_{40}$ or greater ketones having a boiling point of 961° F. or greater). The light products can be removed, as an effluent, from fractional distillation tower via an effluent line. This heavier products fraction can be collected and stored or can undergo further purification in a solvent extraction tower (such as a liquid-liquid extractor) and/or one or more additional distillation tower(s).

Solvent extraction can be used to isolate the aromatics content and/or the amount of polar molecules from hydrocarbons. The solvent extraction process can selectively dissolve aromatic components to form a polar extract phase while leaving the more paraffinic components in a nonpolar phase. Naphthenes can be distributed between the extract and raffinate phases. Typical solvents for solvent extraction can include phenol, furfural, N-methyl pyrrolidone, aliphatic ketones having ~3~6 carbon atoms such as methyl ethyl ketone and methyl isobutyl ketone, low molecular weight hydrocarbons such as propane and butane, benzene, toluene or xylene, or mixtures thereof. The solvents may be mixed with other solvents as such. Any suitable liquid-liquid extractor can be used, such as a counter-current liquid-liquid extractor.

Compositions

Compositions of the present disclosure can include a $C_{40}$-$C_{90}$ wax. Compositions can also include components for personal care products or components used to form candles.

Personal Care Products:

Several personal care products and cosmetics including creams, baby creams, shampoos, body lotions, lipstick, lip and skin ointments etc. make use of microcrystalline waxes. In several such applications use of a $C_{40}$-$C_{90}$ wax of the present disclosure can provide significant advantages. Compositions of such personal care products utilizing microcrystalline waxes have been described in several literature sources including U.S. 2006/0275247, U.S. Pat. No. 4,534,961, WO 2008103817, U.S. Pat. No. 7,138,111, U.S. 2005/0053636, U.S. 2003/016179, the disclosures of which are herein incorporated by reference in their entirety.

In at least one embodiment, a composition includes a mineral oil or an ester oil in addition to a $C_{40}$-$C_{90}$ wax of the present disclosure. The $C_{40}$-$C_{90}$ wax can be present in the composition from about 0.1% by weight to about 99% by weight, such as from about 1% by weight to about 10% by weight based on the total weight of the composition. The mineral oil or ester oil can be present in the composition from about 10% by weight to about 99.9% by weight, such as from about 90% by weight to about 99% by weight, based on the total weight of the composition. An ester oil can be a triglyceride oil, such as caprylic or capric acid. A triglyceride oil can include one or more of olive oil, sunflower oil, soybean oil, peanut oil, rapeseed oil, almond oil, palm oil, coconut oil and palm kernel oil.

The ester oil can be an ester of a carboxylic acid having a chain length of from 3 to 30 carbon atoms and an alcohol having a chain length of from 3 to 30 carbon atoms.

Ester oils can be one or more of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyidodecyl palmitate, oleyl oleate, oleyl erucate, erucyl oleate and erucyl erucate.

In at least one embodiment, a mineral oil is a paraffin oil.

A composition can include one or more additional waxes, in addition to the $C_{40}$-$C_{90}$ wax of the present disclosure. The additional wax can be present in the composition from about 0.1% by weight to about 99% by weight, such as from about 1% by weight to about 10% by weight based on the total weight of the composition. Additional waxes can include triglyceride wax, montan wax, ceresine, a microcrystalline wax, hydroxyoctacosanyl hydroxystearate, beeswax, synthetic beeswax, and a silicone wax.

A composition can further include one or more fatty acid salts of Al, Mg, or Zn, a fatty alcohol, an antioxidant (such as tocopherol), or oil-soluble UV filter substance.

Candles:

In embodiments where a composition is a candle, a $C_{40}$-$C_{90}$ wax of the present disclosure can be a major portion of a candle or a minor portion of a candle. A $C_{40}$-$C_{90}$ wax of the present disclosure present in a candle reduces or prevents migration of colorants, fragrance components and/or other components of the candle to an outer edge (i.e. surface) of the candle. Addition of other migration preventing additives to a candle composition of the present disclosure is therefore optional.

A candle with a string-less wick can be formed by suspending fine granular or powdered material, such as silica gel flour or wheat fiber in a vegetable oil such as soybean oil, cottonseed oil and/or palm oil. The inclusion of particulate material in a candle wax can result in a two phase material and alter the visual appearance of a candle. The candle may also include minor amounts of other additives to modify the properties of the waxy material. Examples of types of additives which may commonly be incorporated into the present candles include colorants, fragrances (e.g., fragrance oils), insect repellants and other migration inhibitors. If the present wax is used to produce a candle, the same standard wicks that are employed with other waxes (e.g., paraffin and/or beeswax) can be utilized.

The present candles may be formed by a method which includes heating the ketone wax to a molten state and introduction of the molten ketone wax into a mold which includes a wick disposed therein. The molten ketone wax is cooled in the mold to solidify the wax.

Alternatively, the present candles may be formed by compression molding. This process is often carried out be introducing wax particles into a mold and applying pressure. The resulting candles may be over-dipped, in the same type or a different type of wax than used in the compression molding process.

Other Waxes:

Solid natural waxes and synthetic waxes may be included in the candle composition. For instance, many creatures (such as insects and animals) and plants form waxy substances that are generally solid at room temperature. Examples include beeswax, lanolin, shellac wax, chinese insect wax, and spermaceti. Some of the examples of the various types of plant waxes are carnauba, candelila, japan wax, ouricury wax, rice-bran wax, jojoba wax, castor wax, bayberry wax, sugar cane wax, and maize wax. Additionally, synthetic waxes may be used. For instance, waxes such as polyethylene wax, Fischer-Tropsch wax, chlorinated naphthalene wax, chemically modified wax, substituted amide wax, alpha olefins and polymerized alpha olefin wax may be used.

A wide variety of coloring and scenting agents, well known in the art of candle making, are available for use with waxy materials. Typically, one or more dyes or pigments is included to provide a desired hue to the color agent, and one or more perfumes, fragrances, essences or other aromatic oils is used to provide the desired odor to the scenting agent. The coloring and scenting agents generally also include liquid carriers which vary depending upon the type of color- or scent-imparting ingredient employed. The use of liquid organic carriers with coloring and scenting agents is preferred because such carriers are compatible with petroleum-based waxes and related organic materials. As a result, such coloring and scenting agents tend to be readily absorbed into waxy materials. It is especially advantageous if a coloring and/or scenting agent is introduced into the waxy material when it is in the form of prilled granules.

A colorant is commonly made up of one or more pigments and dyes. Colorants are typically added in a quantity of about 0.001-2 wt. % of the candle composition. If a pigment is included, it is typically an organic toner in the form of a fine powder suspended in a liquid medium, such as a mineral oil. It may be advantageous to use a pigment that is in the form of fine particles suspended in a vegetable oil, e.g., a natural oil derived from an oilseed source such as soybean or corn oil. The pigment is typically a finely ground, organic toner so that the wick of a candle formed eventually from pigment-covered wax particles does not clog as the wax is burned. Pigments, even in finely ground toner forms, are generally in colloidal suspension in a carrier.

If a dye is utilized, it may be dissolved in an organic solvent. A variety of pigments and dyes suitable for candle making are listed in U.S. Pat. No. 4,614,625, the disclosure of which is herein incorporated by reference. The preferred carriers for use with organic dyes are organic solvents, such as relatively low molecular weight, aromatic hydrocarbon solvents; e.g. toluene and xylene. Since dyes tend to ionize in solution, they are more readily absorbed into the prilled wax granules, whereas pigment-based coloring agents tend to remain closer to the surface of the wax.

Candles often are designed to appeal to the olfactory as well as the visual sense. This type of candle usually incorporates a fragrance oil in the waxy body material. As the waxy material is melted in a lighted candle, there is a release of the fragrance oil from the liquefied wax pool. In at least one embodiment, the scenting agent is an air freshener or an insect repellent.

The air freshener ingredient can be a liquid fragrance comprising one or more volatile organic compounds which are available from perfumery suppliers such IFF, Firmenich Inc., Takasago Inc., Belmay, Noville Inc., Quest Co., and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender. Orange, Origanum, Petitgrain, White Cedar, Patchouli, Lavandin, Neroli, Rose and the like.

A wide variety of chemicals are known for perfumery such as aldehydes, ketones, esters, alcohols, terpenes, and the like. A fragrance can be relatively simple in composition, or can be a complex mixture of natural and synthetic chemical components.

Synthetic types of fragrance compositions either alone or in combination with natural oils can include those described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like. The scenting agent can also be a liquid formulation containing an insect repellent such as citronellal, or a therapeutic agent such as eucalyptus or menthol. Once the coloring and scenting agents have been formulated, the desired quantities are combined with waxy material, such as a $C_{40}$-$C_{90}$ ketone wax of the present disclosure and optionally one or more additional waxes, which will be used to form the body of the candle. For example, the coloring and/or scenting agents can be added to the waxy materials in the form of prilled wax granules. When both coloring and scenting agents are present in a candle composition, it is generally preferable to combine the agents together and then add the resulting mixture to the wax. It is also possible, however, to add the agents separately to the waxy material. Having added the agent or agents to the wax, the granules are coated by agitating the wax particles and the coloring and/or scenting agents together. The agitating step commonly consists of tumbling and/or rubbing the particles and agent(s) together. Preferably, the agent or agents are distributed substantially uniformly among the particles of wax, although it is entirely possible, if desired, to have a more random pattern of distribution. The coating step may be accomplished by hand, or with the aid of mechanical tumblers and agitators when relatively large quantities of prilled wax are being colored and/or scented.

A $C_{40}$-$C_{90}$ ketone wax of the present disclosure can be a minor component of a candle, e.g. as an additive that reduces or prevents migration of colorants, fragrance components, and/or other components toward an outer edge (surface) of the candle. In at least one embodiment, a candle composition may include 0.1 wt % to 5.0 wt % of a migration inhibitor, such as a $C_{40}$-$C_{90}$ ketone wax and/or one or more additional migration inhibitors. One type of compound which can act as a migration inhibitor includes polymerized alpha olefins, more particularly polymerization products formed alpha olefins having at least 10 carbon atoms and, more commonly from one or more alpha olefins having 10 to about 25 carbon atoms. One suitable example of such as polymer is an alpha olefin polymer sold under the tradename Vybar® 103 polymer (mp 168° F. (circa 76° C.); available from Baker-Petrolite, Sugarland, Tex.). The inclusion of sorbitan triesters, such as sorbitan tristearate and/or sorbitan tripalmitate and related sorbitan triesters formed from mixtures of fully hydrogenated fatty acids, in the present waxes may also decrease the propensity of colorants, fragrance components and/or other components of the wax to migrate to the candle surface. The inclusion of either of these types of migration inhibitors can also enhance the flexibility of the base wax material and decrease its chances of cracking during the cooling processes that occurs in candle formation and after extinguishing the flame of a burning candle.

EXAMPLES

Example 1

—Forming Oligomerized Product by Sequential Processing of Soybean Oil

Figure 3:
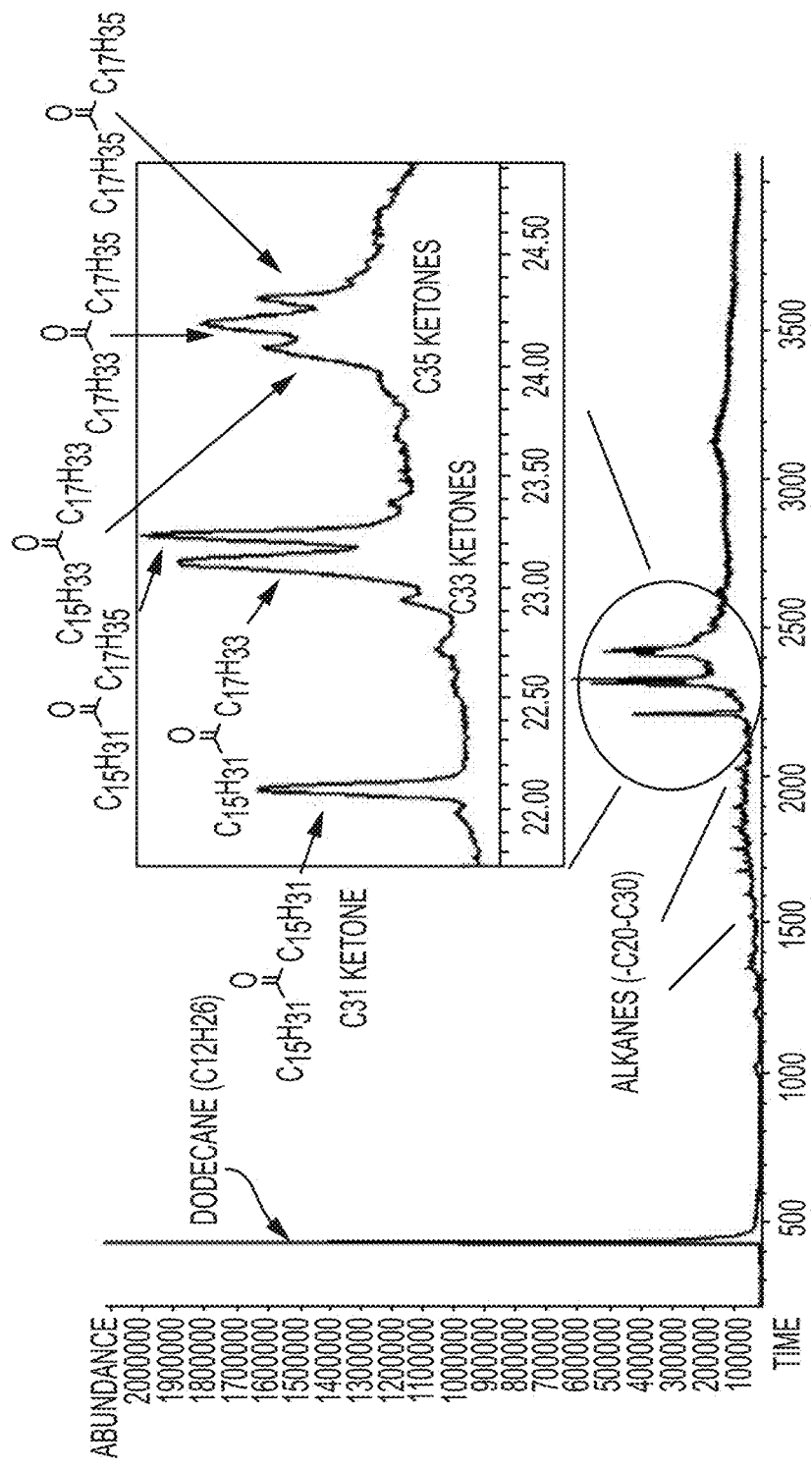
FIG. 3 is a gas chromatography/mass spectrometry plot of product distribution in a product mixture, according to one embodiment.

About 2.5 g of soybean oil were reacted over about 0.4 g of Pural® MG hydrotalcite (MgO:$Al_2O_3$≈63/37) at about 325° C. and a partial pressure of hydrogen of about 400 psig (~2.8 MPag) for about 24 hours under batch processing conditions. The soybean oil appeared to be completely converted. FIG. 3 is a gas chromatography/mass spectrometry plot of the product distribution in the product mixture formed from the reaction. The product mixture contained about 34 wt % olefins and paraffins. The product mixture also appeared to contain about 8 wt %, 25 wt %, and 33 wt % of $C_{31}$, $C_{33}$, and $C_{35}$ ketones, respectively. Based on the natural distribution of fatty acids in soybean oil, the majority of compounds in the product contained unsaturated double bonds.

The product mixture was then further coupled in the presence of an acidic catalyst under coupling conditions to form various oligomers having $C_{40}$-$C_{90}$ ketone waxes. About 2 g of the product mixture was reacted over about 0.4 g of MCM-49 at about 300° C. and a partial pressure of hydrogen of about 400 psig (~2.8 MPag) for about 24 hours.

Figure 4:
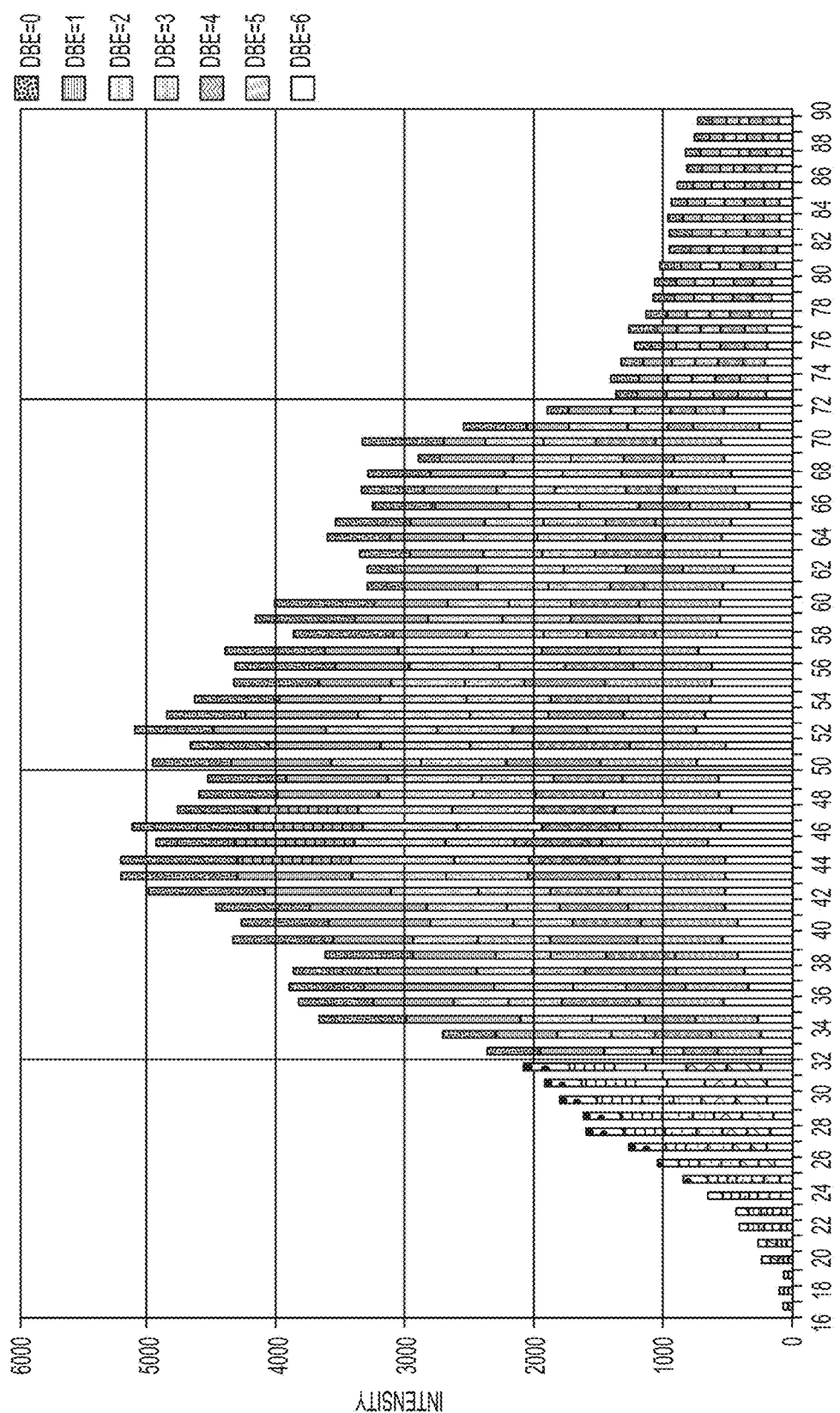
FIG. 4 is a graph illustrating Field desorption-time of flight (FD-TOF) mass spectrometry characterization and double bond equivalent (DBE) content of an oligomerized product, according to one embodiment.

FIG. 4 is a graph illustrating field desorption-time of flight (FD-TOF) mass spectrometry characterization of the resulting oligomerized product formed during oligomerization, as well as the double bond equivalent (DBE) values for each carbon chain length in the oligomerized product. To determine the carbon chain length from the FD-TOF data, it was assumed that the product was free of heteroatoms. For products that corresponded to dimers, trimers, or tetramers from coupling of ketones, approximately 2, 3, or 4 carbons, respectively, were subtracted from the chain length. FIG. 4 shows that the resulting oligomerized product had a roughly Gaussian distribution of carbon chain lengths. Additionally, FIG. 4 shows that less than about 30 wt % (based on the total intensity) of the products for each carbon chain length had a DBE value of 6; that less than about 20 wt % of the products for each carbon chain length had a DBE value of 5; and that less than about 20 wt % of the products for each carbon chain length had a DBE value of 4.

Example 2

—Forming Oligomerized Product by Single Step Processing of Soybean Oil

In this Example, about 2.5 g of soybean oil were reacted over a mixture of MCM-49 and hydrotalcite at about 300° C. and a partial pressure of hydrogen of about 400 psig (~2.8 MPag) for about 24 hours under batch processing conditions. The soybean oil appeared to be completely converted.

Figure 5:
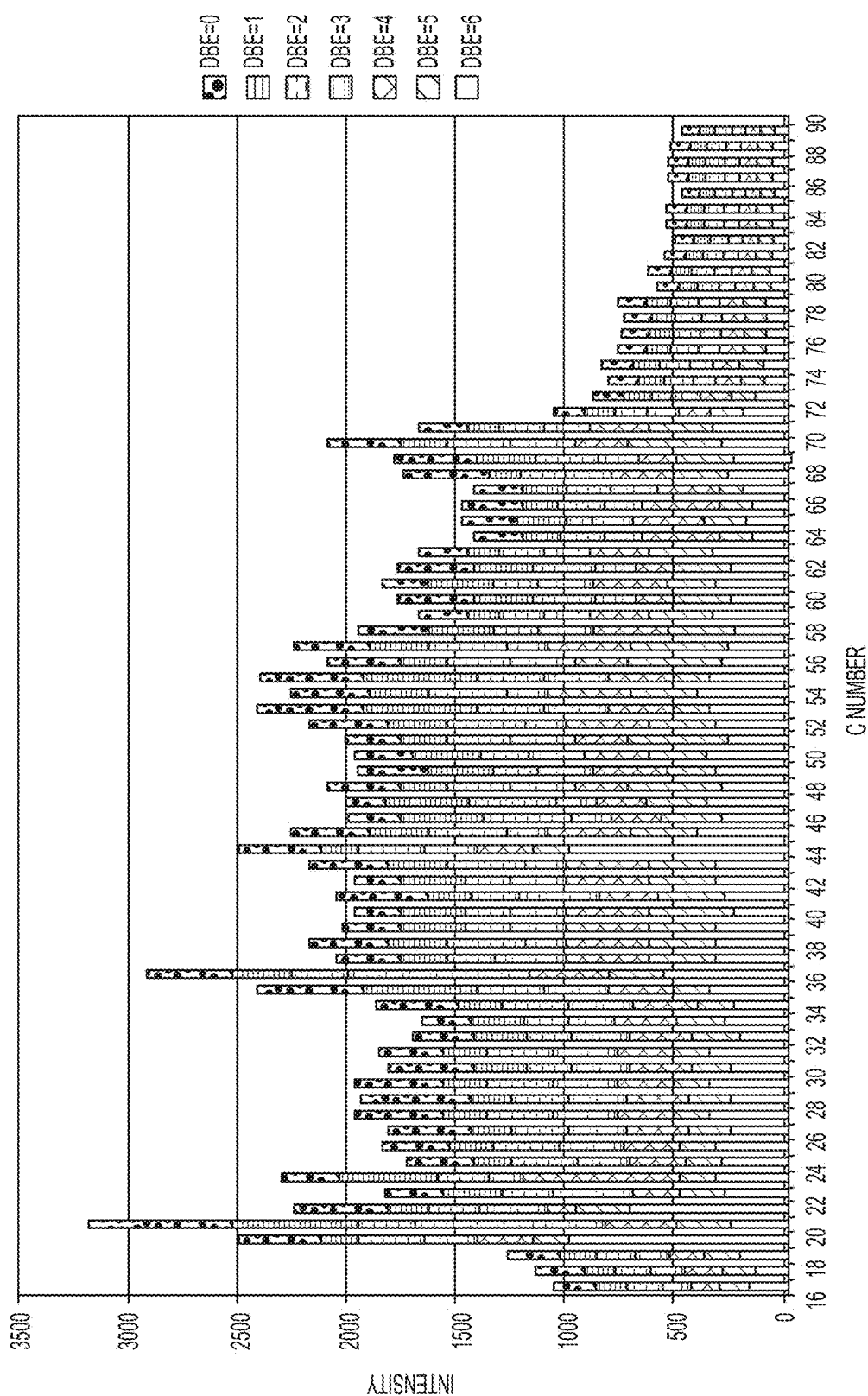
FIG. 5 is a graph illustrating the FD-TOF mass spectrometry characterization and double bond equivalent (DBE) content of an oligomerized product, according to one embodiment.

FIG. 5 is a graph illustrating the FD-TOF results from single step processing of the soybean oil in the presence of both an acidic and a basic catalyst. The resulting product mixture does not produce a Gaussian distribution of carbon chain lengths. Instead, the intensity for carbon chain lengths closer to the chain lengths present in the original soybean oil feed appeared to be similar to the intensity for dimers and trimers formed from the soybean oil. The intensity then appeared to fall off for carbon chain lengths corresponding to tetramers (or higher oligomers). Additionally, FIG. 5 appears to show that less than about 45 wt % (based on the total intensity) of the products for each carbon chain length had a DBE value of 6; that less than about 20 wt % of the products for each carbon chain length had a DBE value of 5; and that less than about 20 wt % of the products for each carbon chain length had a DBE value of 4.

Boiling Points

Example 1

Figure 6:
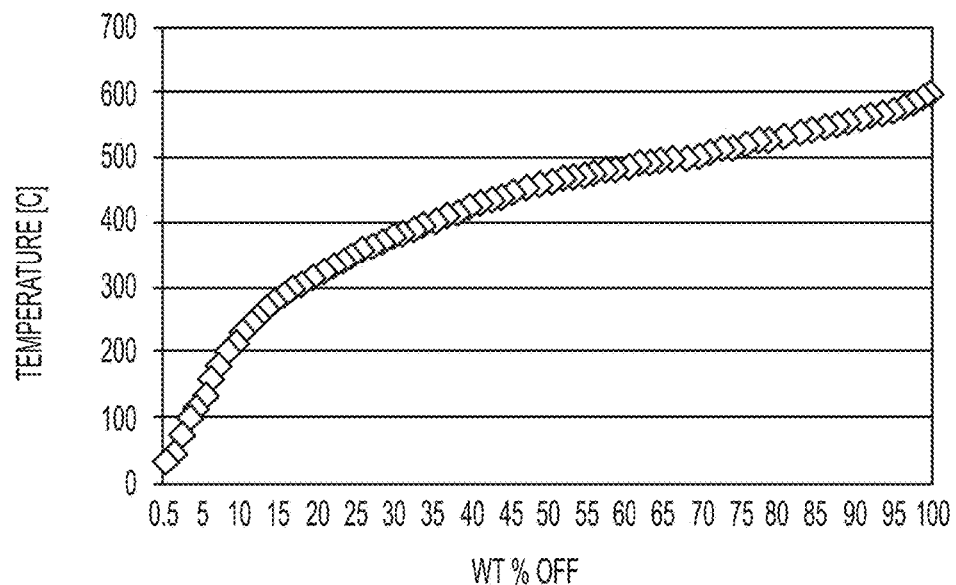
FIG. 6 is a graph illustrating the boiling points of the ketone waxes of Example 1, according to one embodiment.

FIG. 6 is a graph illustrating the boiling points of the ketone waxes of Example 1. "% off" indicates the wt % of ketone waxes that have distilled by the temperature indicated on the x-axis, based on the total weight of the ketone wax sample. As shown in FIG. 6, 31 wt % of the total product has a boiling point above 500° C., while 17% has a boiling point below 300° C. and 53% has a boiling point between 300° C. and 500° C.

Example 2

Figure 7:
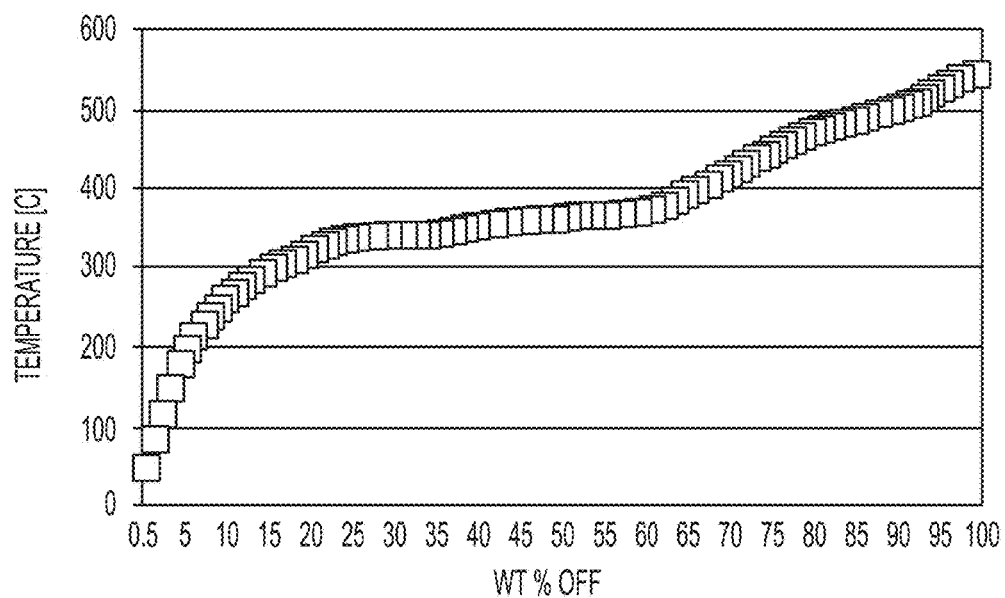
FIG. 7 is a graph illustrating the boiling points of the ketone waxes of Example 2, according to one embodiment.

FIG. 7 is a graph illustrating the boiling points of the ketone waxes of Example 2. "% off" indicates the wt % of ketone waxes that have distilled by the temperature indicated on the x-axis, based on the total weight of the ketone wax sample. As shown in FIG. 7, 10 wt % of the total product has a boiling point above 500° C. while 17% has a boiling point below 300° C. and 73% has a boiling point between 300° C. and 500° C.

Two-Dimensional Gas Chromatography

Comprehensive two-dimensional gas chromatography (GC×GC) is a separation technique developed in recent years. It can provide improved chromatographic resolution of complex mixtures. GC×GC uses a single GC unit containing two separation columns of different selectivity. A modulation unit situated between these two separation columns performs solute focusing and re-injection into a short, high-speed second column. GC×GC may be considered as a 'continuous' heart-cutting form of a conventional single heart-cutting multidimensional GC that has been established for many years.

These advances have enabled GC×GC to become an ideal technique for analyzing mixtures, such as base stocks. One advantage of the GC×GC technique is its enhanced sensitivity due to the re-focusing process during the modulation operation. Another advantage of the GC×GC technique is the qualitative analysis through compound class separation. Hence, in addition to single component separation, it also provides the compound class homologous series trend information. This trend information can be further combined with the reference standard compounds or corresponding GC-MS data to greatly improve the capability of elucidation of individual molecular structure in the complex mixtures.

Figure 8:
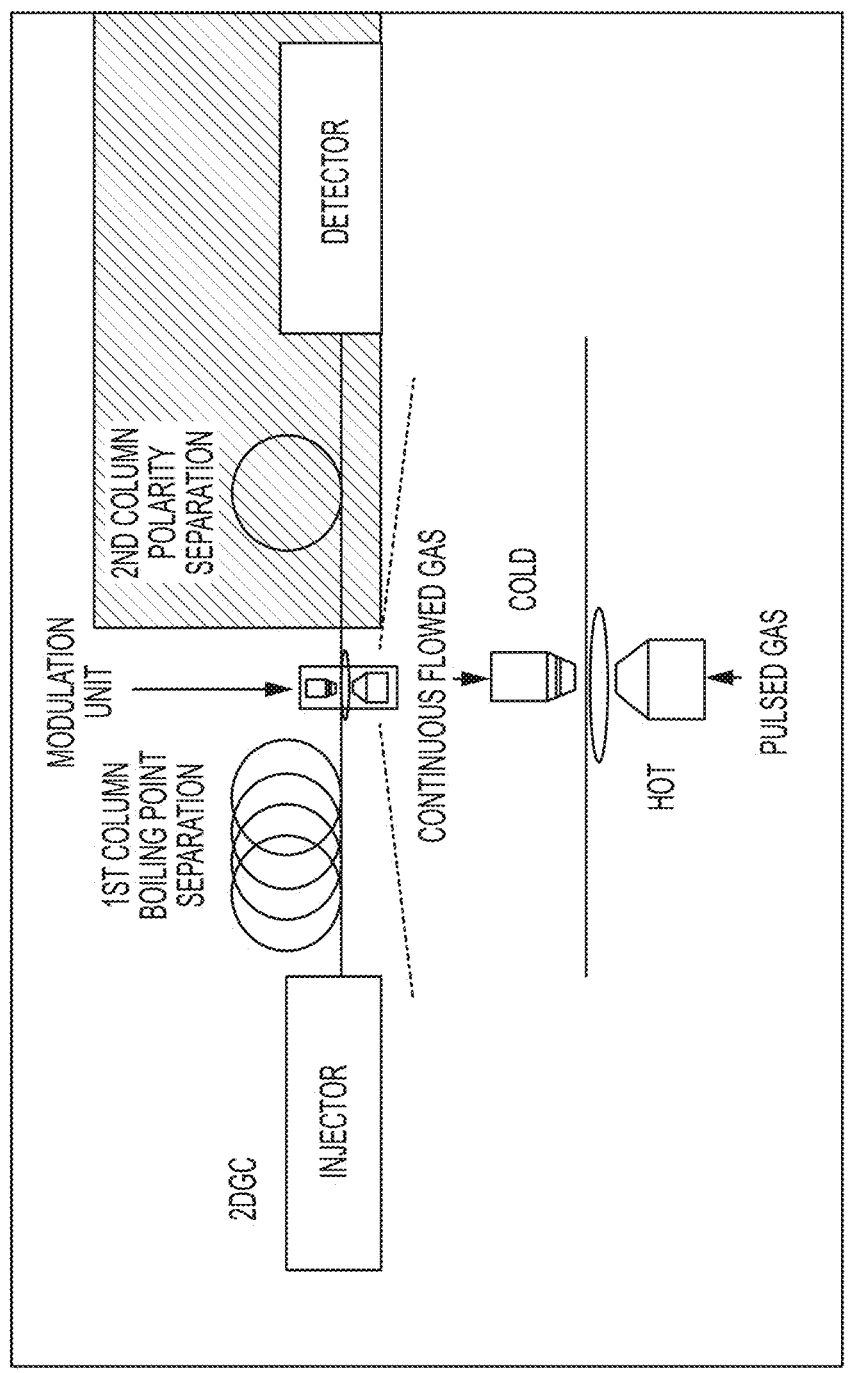
FIG. 8 is a schematic illustration of a 2-dimensional gas chromatograph configuration, according to one embodiment.

The 2DGC (GC×GC) system consists of an Agilent 6890 gas chromatograph (Agilent Technology, Wilmington, Del.) configured with inlet, columns, and detectors, shown in FIG. 8. A split/splitless inlet system with a 100 sample position tray autosampler was used. The two-dimensional capillary column system utilizes a non-polar first column (BPX-5, 30 meter, 0.25 mm I.D., 1.0 micron film), and a polar (BPX-50, 2 meter, 0.25 mm I.D., 0.25 micron film), second column. Both capillary columns are the products of SGE Inc. (Austin, Tex.). A looped thermal modulation assembly based on Zoex technology (Zoex Corp. Lincoln. Nebr.), which is liquid nitrogen cooled "trap-release" looped thermal modulator, is installed between these two columns. A flame ionization detector (FID) is used for the signal detection. A 0.2 microliter sample was injected with 50:1 split at 300° C. inlet temperature. Carrier gas flow was ramped based on the head pressure. The head pressure is programmed from 24 psi with 0-minute hold and 0.2 psi per minute increment to 42 psi with 0-minute hold. The oven was programmed from 190° C. with 0-minute hold and 2.0° C. per minute increment to 370° C. with 0-minute hold. The hot jet was programmed from 240° C. with 0-minute hold and 2.0° C. per minute increment to 390° C. with 15-minute hold. The total GC run time was 90 minutes. The modulation period was 10 seconds. The sampling rate for the detector was 100 Hz.

FIG. 8 is a schematic illustration of a GC×GC configuration. After data acquisition, the data were processed for qualitative and quantitative analysis. The qualitative analysis converted data to a two-dimensional image that was processed by a commercial program ("Transform", Research Systems Inc. Boulder, Colo.). The two-dimensional image was further treated by "Photoshop" program (Adobe System Inc. San Jose, Calif.) to generate publication-ready images. Peak volumes were then quantified.

The two-dimensional chromatographic separation is a combination of non-polar column separation (1st column, X-axis) and polar column separation (2nd column, Y-axis). The non-polar column separation is based on the boiling point of the component in the sample mixture, which closely correlated to the carbon chain length. It can also be viewed as a boiling point separation. The polar column separation is based on the polarity of the component in the sample mixture, which closely correlated to the functional groups on the component. It can also be viewed as a compound class separation. With this detailed two-dimensional separation, the separated complex mixture can be systematically, qualitative and quantitative analyzed.

In addition to the qualitative analysis, the GC×GC technique also provides advantages in the quantitative analysis for complex mixtures than traditional GC. Because the GC×GC offers better separation for individual components, better-defined peak integrations and more accurate quantification are obtained. This improved quantitative analysis gives more accurate compositional information for complex mixtures such as the waxes of the present disclosure.

A sample is injected into an inlet device connected to the inlet of a first column to perform a first dimension separation. Sample injection may be by any known sample injection device such as a syringe. The sampling device may hold a single sample or may hold multiple samples for injection into the first column. The column contains a stationary phase that is usually the column coating material. The first column may be coated with a non-polar material. When the column coating material is methyl silicon polymer, the polarity can be measured by the percentage of methyl group substituted by the phenyl group. The polarity of coating materials are measured on a % of phenyl group substitution scale from 0 to 100 with zero being non-polar and 80 (80% phenyl substitution) being considered as polar. These methyl silicon polymers are considered non-polar and have polarity values in the range from 0 to 20. Phenyl substituted methyl silicon polymers are considered semi-polar and have polarity values of 21 to 50. Phenyl substituted methyl silicon polymers coating materials have been called polar materials when greater than 50% phenyl substitution group is included in polymers. Other polar coating polymers, such as carbowaxes, were also used in chromatographic applications. Carbowaxes are high molecular weight polyethylene glycols. In addition, a series of Carborane Silicon polymers sold under the trade name Dexsil have been especially designed for high temperature applications.

The first column coated with a non-polar material provides a first separation of the sample. The first separation, also known as the first dimension, generates a series of bands over a given time period. This first dimension chromatograms is not like the chromatogram that could be obtained from a conventional chromatogram. The bands represent individual components or groups of components of the sample injected, and separated or partially overlapping with adjacent bands. When the complex mixture is separated by the first dimension column, it still has many co-elutions that are not able to be separated by the first dimension column. The bands of separated materials from the first dimension are then sent in their entirety to the second column to perform a further separation, especially of the co-eluted components. This further separation is referred to as a second dimension. The second dimension is a second column coated with a semi-polar or polar material, preferably a semi-polar coating material.

A modulator manages the flow and separation timing between the end of the first column and the beginning of the second column. A modulator may be a thermal modulator that uses a trap/release mechanism. In this mechanism, cold nitrogen gas is used to trap a separated sample from the first dimension followed by a periodic pulse of hot nitrogen to release trapped sample to a second dimension. Each pulse is analogous to a sample injection into the second dimension. The role of the modulator is (1) collect the continuous eluent flow out from the end of the first column with a fixed period of time (modulated period), and (2) inject collected eluent to the beginning of the second column by releasing collected eluent at the end of modulated period. The function of the modulator is (1) define the beginning time of a specific second dimensional column separation and (2) define the length of the second dimensional separation (modulation period). The separated bands from the second dimension are coupled with the bands from the first dimension to form a comprehensive 2D chromatogram. The bands are placed in a retention plane wherein the first dimension retention times and the second dimension retention times form the axes of the 2D chromatogram.

For example, a conventional GC experiment takes 110 minutes to separate a mixture (a chromatogram with 110 minutes retention time, x-axis). When the same experiment is performed under 2D GC conditions with a 10 second modulation period, it will become 480 chromatograms (60 seconds times 80 minutes divided by 10 seconds) where each 10 second chromatogram (y-axis) lines up one-by-one along the retention time axis (x-axis). In 2D GC, the x-axis is the first dimension retention time (the same as conventional GC), the y-axis is the second dimensional retention time, and the peak intensity should stick out in the third dimension z-axis. In order to express this 3D picture on two dimensional plots, the intensity has been converted based on a pre-defined gray scale table to express their relative peak intensity by gray-scale.

The data point format of total product 2DGC/FID (flame ionization detector) run is 660×1000. Separation column set used is: 1st Column, SGE BPX-5 (BPX is a phenyl siloxane polymer), 30 meter, 0.25 mm I.D., 1.0 micrometer Film and 2nd Column. SGE BPX-50, 3.0 meter, 0.25 mm I.D., 0.25 micrometer Film. Oven temperature program was set at 60° C. for 0.0 minutes and ramped at 3.0° C. per minute to 390° C. for 0.0 minutes. Flow program is constant flow at 2.0 ml per minute for entire experiment. The inlet temperature was set at 360° C. with split ratio of 50:1. The sample injection volume is 0.2 microliter.

The data point format of reference petroleum wax 2DGC/FID (flame ionization detector) run is 660×1000. Separation column set used is: 1st Column, SGE BPX-5 (BPX is a phenyl siloxane polymer), 30 meter, 0.25 mm I.D., 1.0 micrometer Film and 2nd Column, SGE BPX-50, 9.0 meter, 0.25 mm I.D., 0.25 micrometer Film. Oven temperature program was set at 170° C. for 0.0 minutes and ramped at 2.0° C. per minute to 390° C. for 0.0 minutes. Flow program is constant flow at 2.0 ml per minute for an entire experiment. The inlet temperature was set at 360° C. with split ratio of 50:1. The sample injection volume is 0.2 microliter.

Figure 9A:
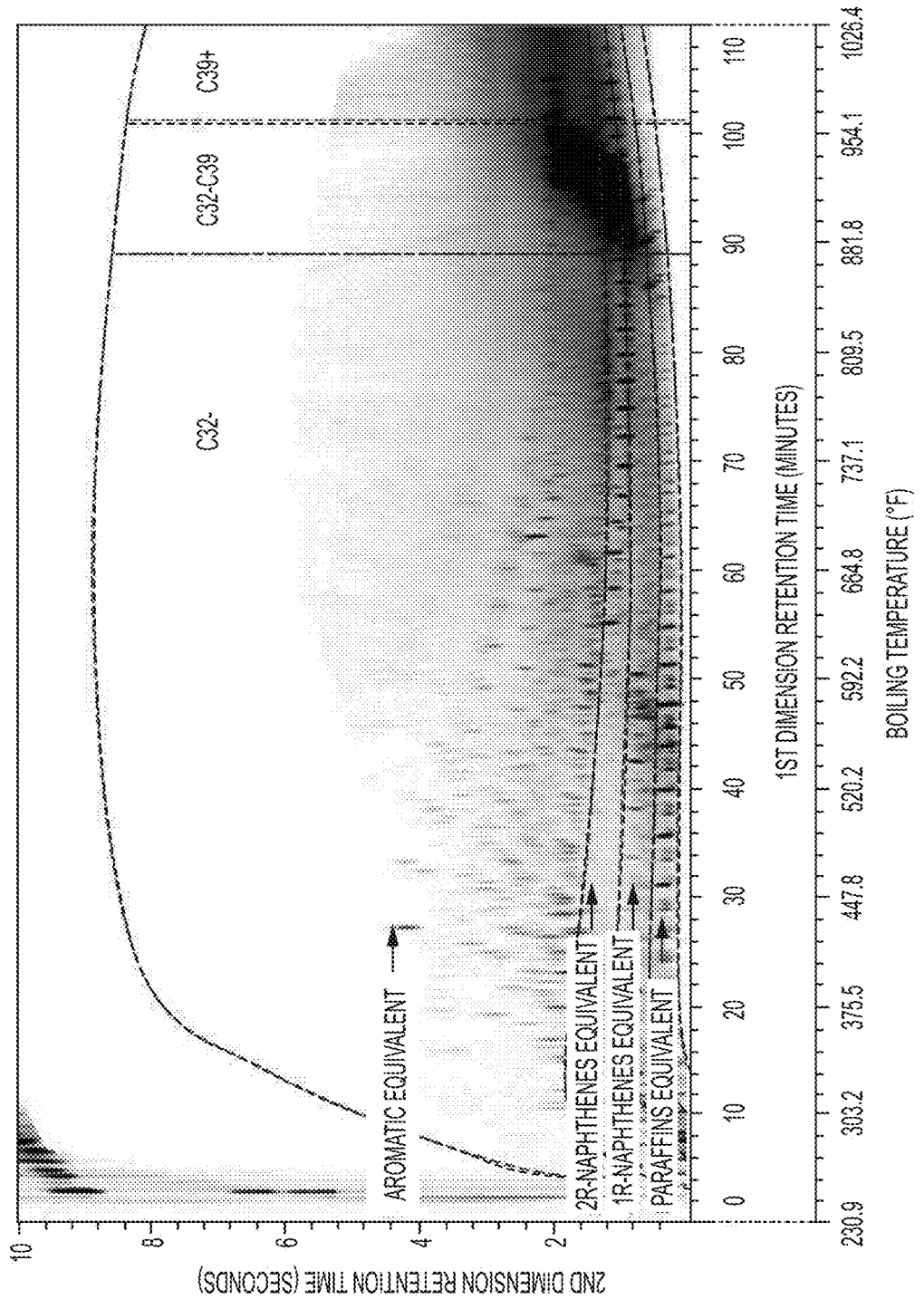
FIG. 9A is a 2-dimensional gas chromatography chromatogram of the product of Example 1, according to one embodiment.
Figure 9B:
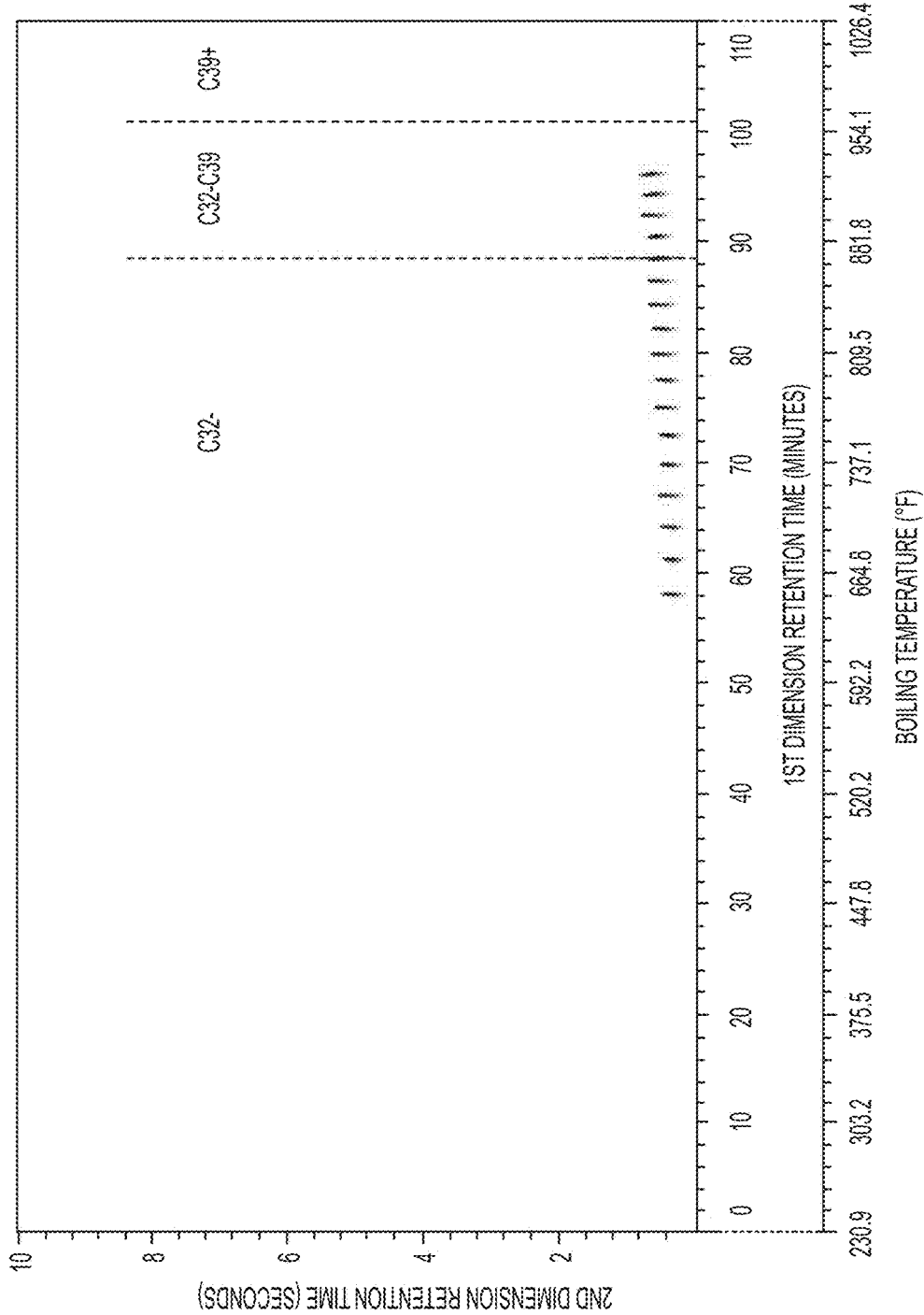
FIG. 9B is a 2-dimensional gas chromatography chromatogram of normal paraffin mixtures from carbon chain length 20 to 36, according to one embodiment.
Figure 10A:
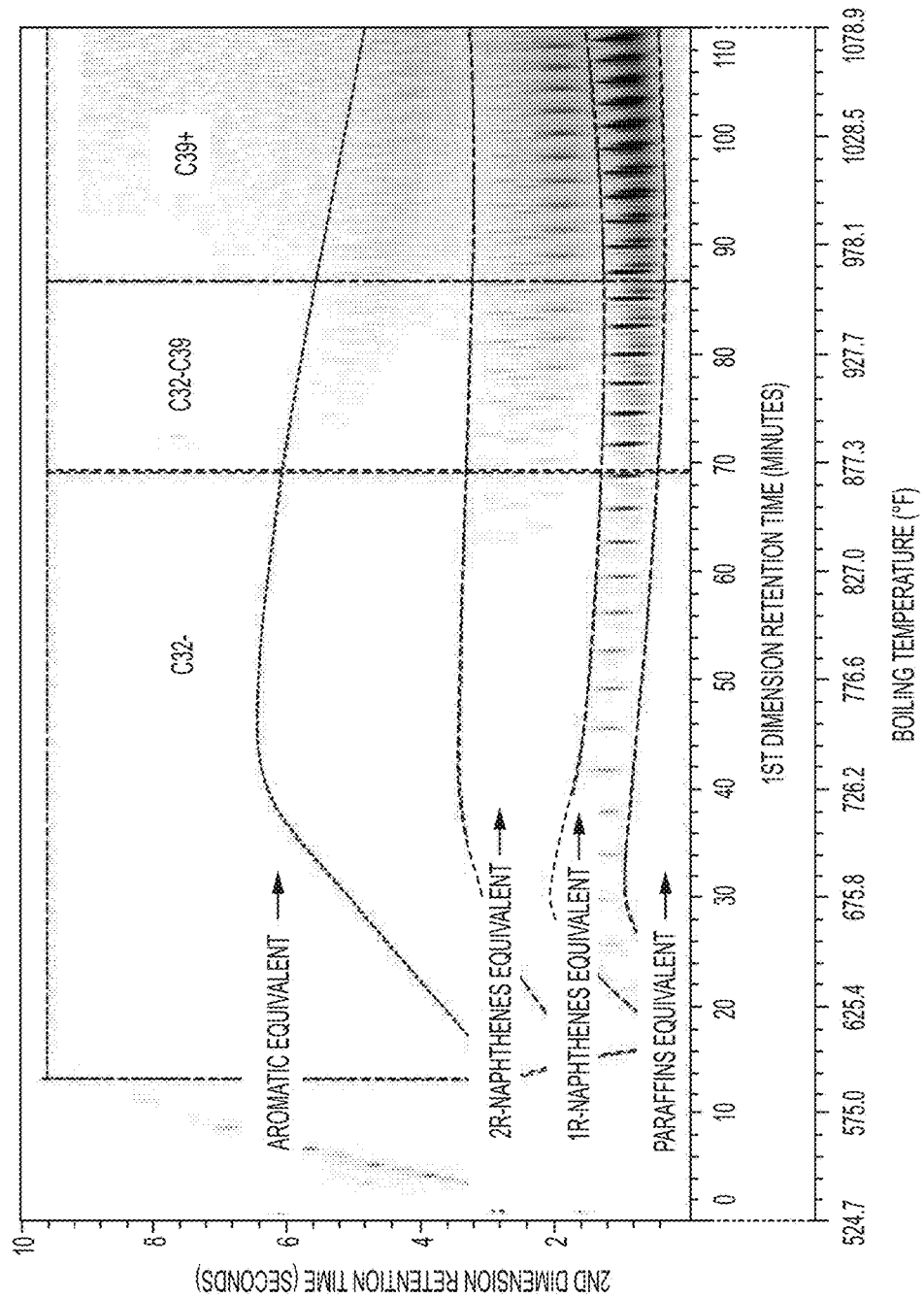
FIG. 10A is a 2-dimensional gas chromatography chromatogram of a petroleum wax, according to one embodiment.
Figure 10B:
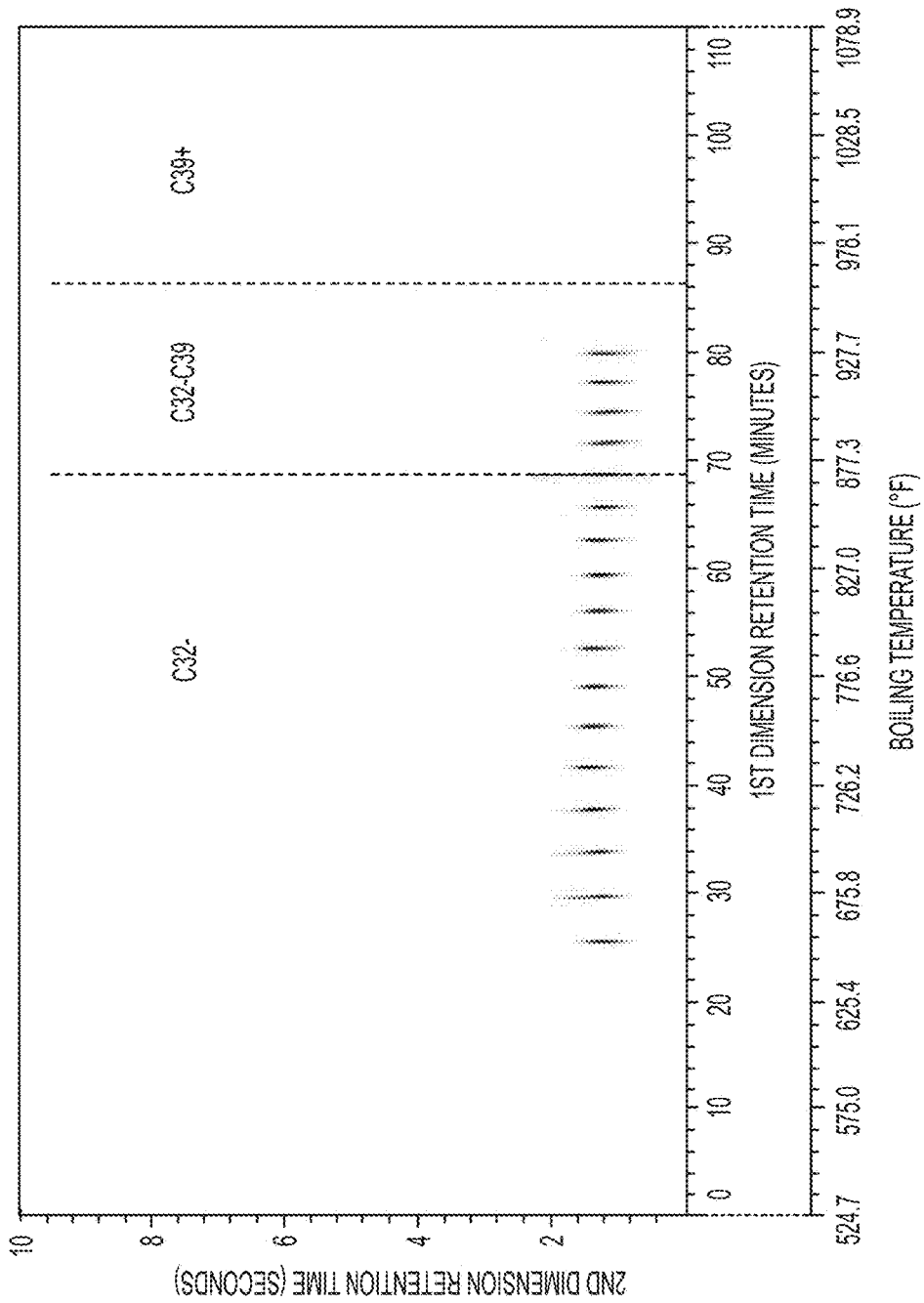
FIG. 10B is a 2-dimensional gas chromatography chromatogram of normal paraffin mixtures from carbon chain length 20 to 36, according to one embodiment.

FIG. 9A is the 2DGC chromatogram of the total product from Example 1 and FIG. 10A is the 2DGC chromatogram of a petroleum wax serving as comparison. The X-axis retention time in both 2DGC chromatograms can be converted to a boiling temperature scale if a normal paraffin mixture sample is run under the same 2DGC conditions. FIG. 9b and FIG. 10b show the 2DGC chromatograms of normal paraffin mixtures from carbon chain length 20 to 36 under the same as total product and petroleum wax conditions. The linear correlation can be found based on the normal paraffin retention time and well-known boiling temperature of those normal paraffins. The retention time then can be converted based on this correlation and is shown in FIGS. 9A to 10B. Based on the polarity separation on the y-axis, the composition of paraffin-equivalent, one-ring naphthene equivalent, two-ring naphthene equivalent, and aromatic equivalent can also be determined.

In the case of hydrocarbons containing no heteroatom, the paraffin equivalent means fully saturated hydrocarbons; one-ring (1R) naphthene equivalent can include one saturated ring or one C=C double bond in the molecules: two-ring (2R) naphthene equivalent refers to molecules containing two saturated cyclic rings (which can be fused or separated by C—C bonds), one saturated ring plus one C=C double bond, or two C=C double bonds: while aromatic equivalent means molecules containing any kind of aromatic rings. When a heteroatom (such as oxygen) is presence, depending on the form of the functional group, such as ketone, the molecules will move up at higher positions on the Y-axis of the 2DGC plot, showing in the one-ring naphthene equivalent, two-ring naphthene equivalent, and aromatic equivalent regions. The 2DGC plot of the total product in Example 1 is consistent with the FD-TOF MS data (FIG. 4), revealing presence of ketone functional groups.

Based on the FIG. 9A, the total product has a high abundance group of molecules around retention time 88 minutes to 100 minutes (or equivalent to boiling temperatures of normal paraffin with chain length $C_{32}$ and $C_{39}$). In order to demonstrate the composition difference between total product and the petroleum wax reference, divided guide lines have been used (e.g., on the X-axis, there were $C_{32}$ and $C_{39}$ normal paraffin boiling temperature and on the Y-axis, there were the paraffin-equivalent, one-ring naphthene equivalent, two-ring naphthene equivalent, and aromatic equivalent). An integration of detected signal based on these temperature cuts as well as marked polarity separation, the total product and reference petroleum wax can be clearly distinguished based on the composition (molecule distribution). Table 2 illustrates composition comparison between the total product from Example 1 and petroleum wax based on the component boiling temperature.

TABLE 2

| | Weight Percentage | | | | | |
|---|---|---|---|---|---|---|
| | Total Product | Petroleum Wax | Total Product | Petroleum Wax | Total Product | Petroleum Wax |
| Boiling Temperature | 871° F.< | | 871° F.-961° F. | | >961° F. | |
| Carbon Number equivalent | C32- | | C32-39 | | C39+ | |
| Paraffins equivalent | 6.04% | 1.79% | 0.67% | 9.21% | 0.23% | 40.67% |
| 1R-Naphthenes equivalent | 11.06% | 0.04% | 4.14% | 2.50% | 0.86% | 18.80% |
| 2R-Naphthenes equivalent | 7.02% | 0.00% | 7.48% | 10.07% | 1.26% | 9.69% |
| 1R-Aromatics equivalent | 27.24% | 0.00% | 20.70% | 3.61% | 13.30% | 3.61% |

Overall, $C_{40}$-$C_{90}$ ketone waxes of the present disclosure have a unique polarity with an oxygen content that is higher than that of a petroleum derived wax but significantly lower than state of the art renewable ester based waxes. The unique oxygen content provides a ketone wax with a polarity that cannot be obtained from a petroleum derived wax or the state of the art renewable ester based waxes. A branched ketone wax with a carbon chain length distribution of $C_{40}$-$C_{90}$ can be obtained by distillation of the products. $C_{40}$-$C_{90}$ ketone waxes of the present disclosure are ester based with much higher oxygen content and lower carbon chain lengths. Thus, the carbon chain lengths of $C_{40}$-$C_{90}$ ketone waxes of the present disclosure are more similar to a petroleum based petrolatum wax. However, petrolatum waxes have very low polarities due to their paraffinic nature. The ketonic nature of $C_{40}$-$C_{90}$ ketone waxes of the present disclosure offer increased polarity over petrolatum waxes. The increased polarity provides improved performance in many areas where petrolatum waxes are currently applied, particularly in applications such as coatings and candles where interaction with either a polar substrate or polar fragrances. $C_{40}$-$C_{90}$ ketone waxes of the present disclosure with any percentage of the ketone in the composition can be advantageous to use in coating applications particularly coating of polar substrates, including use in cosmetics and personal care products. Furthermore use of such waxes as additives in candles may also enhance the capability to hold and disperse aromatic and polar fragrance molecules with reduced or eliminated migration in such candles.

When numerical lower limits and numerical upper limits are listed herein, ranges from any lower limit to any upper limit are contemplated. While the illustrative embodiments of the present disclosure have been described with particularity, it will be understood that various other modifications will be apparent to and can be readily made by those skilled in the art without departing from the spirit and scope of the present disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the embodiments of the present disclosure pertain.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A polar ketone wax comprising:
   about 50 wt % or greater C40-C90 ketone content;
   about 50 wt % or greater of the polar ketone wax has a boiling point of 961° F. or greater; and
   a paraffins content of less than about 10 wt %, as determined by 2-dimensional gas chromatography.

2. The polar ketone wax of claim 1, wherein the polar ketone wax has a 1R-naphthene equivalent of from about 0.1 wt % to about 20 wt %, as determined by 2-dimensional gas chromatography.

3. The polar ketone wax of claim 1, wherein the polar ketone wax has a 1R-naphthene equivalent of from about 1 wt % to about 10 wt %, as determined by 2-dimensional gas chromatography.

4. The polar ketone wax of claim 1, wherein the polar ketone wax has a paraffins content of from about 0 wt % to about 5 wt %, as determined by 2-dimensional gas chromatography.

5. The polar ketone wax of claim 1, wherein the polar ketone wax has a 2R-naphthene equivalent of from about 0.1 wt % to about 20 wt %, as determined by 2-dimensional gas chromatography.

6. The polar ketone wax of claim 1, wherein the polar ketone wax has a 2R-naphthene equivalent of from about 5 wt % to about 10 wt %, as determined by 2-dimensional gas chromatography.

7. The polar ketone wax of claim 1, wherein the polar ketone wax has a 1R-aromatic equivalent of from about 50 wt % to about 99.9 wt %.

8. The polar ketone wax of claim 1, wherein the polar ketone wax has a 1R-aromatic equivalent of from about 80 wt % to about 90 wt %.

9. The polar ketone wax of claim 1, wherein the polar ketone wax has a double bond equivalent value from 1 to about 6.

10. The polar ketone wax of claim 9, wherein less than about 30 wt % of the polar ketone wax has a double bond equivalent value of 6.

11. The polar ketone wax of claim 9, wherein less than about 20 wt % of the polar ketone wax has a double bond equivalent value of 5.

12. The polar ketone wax of claim 9, wherein less than about 20 wt % of the polar ketone wax has a double bond equivalent value of 4.

13. The polar ketone wax of claim 1, wherein the polar ketone wax has an oxygen content of from about 1 wt % to about 15 wt %.

14. The polar ketone wax of claim 13, wherein the polar ketone wax has an oxygen content of from about 4 wt % to about 8 wt %.

15. The polar ketone wax of claim 1, wherein the polar ketone wax has about 80 wt % or greater C40-C90 ketone content.

16. The polar ketone wax of claim 15, wherein the polar ketone wax has about 95 wt % or greater $C_{40}$-$C_{90}$ ketone content.

17. The polar ketone wax of claim 1, wherein about 95 wt % or greater of the polar ketone wax has a boiling point of 961° F. or greater.

18. The polar ketone wax of claim 1, wherein the polar ketone wax has a kinematic viscosity at 100° C. of from about 3.0 cSt to about 7.5 cSt.

19. The polar ketone wax of claim 1, wherein the polar ketone wax has a melting point of about 78° C. or greater, as determined by differential scanning calorimetry.

20. A candle, coating, or personal care product comprising the polar ketone wax of claim 1.

21. A method for forming a polar ketone wax, said method comprising the steps of:
   a) exposing a feed stock to a basic catalyst under conditions suitable for coupling unsaturated carbon chains from the feed stock to form a composition including a ketone wax;
   b) oligomerizing the ketone wax over an acidic catalyst under conditions suitable to form an oligomerized ketone wax having $C_{40}$-$C_{90}$ ketone wax; and
   c) distilling and/or extracting the oligomerized ketone wax to provide a polar ketone wax having $C_{40}$-$C_{90}$ ketone wax.

22. The method of claim 21, wherein the basic catalyst of step a) comprises at least 5 wt % of a rare earth metal salt, an alkali metal salt, or an alkaline earth metal salt relative to a total catalyst weight.

23. The method of claim 21, wherein the conditions of step a) comprise a temperature of from about 300° C. to about 450° C. and a hydrogen partial pressure of from about 1.8 MPag to about 35 MPag.

24. The method of claim 21, wherein the acidic catalyst of step b) comprises a molecular sieve, metalloaluminophosphate, amorphous aluminosilicate, cationic acidic clay, or a mixture thereof.

25. The method of claim 21, wherein the conditions of step b) comprise a temperature of from about 150° C. to about 450° C., a liquid hourly space velocity of from about 0.1 v/v/hour to about 10 v/v/hour, and a hydrogen partial pressure of from about 1.8 MPag to about 35 MPag.

26. The method of claim 21, wherein steps a) and b) are performed concurrently in the same reaction environment.

* * * * *